United States Patent [19]
Bishop et al.

[11] Patent Number: 5,661,152
[45] Date of Patent: Aug. 26, 1997

[54] TRICYCLIC SULFONAMIDE COMPOUNDS USEFUL FOR INHIBITION OF G-PROTEIN FUNCTION AND FOR TREATMENT OF PROLIFERATIVE DISEASES

[75] Inventors: W. Robert Bishop, Pompton Plains; Ronald J. Doll, Maplewood; Alan K. Mallams, Long Valley; F. George Njoroge, Union; Joanne M. Petrin, Cedar Grove; John J. Piwinski, Clinton Township, all of N.J.

[73] Assignee: Schering Corporation, Kenilworth, N.J.

[21] Appl. No.: 444,996

[22] Filed: May 19, 1995

Related U.S. Application Data

[63] Continuation of Ser. No. 312,350, Sep. 26, 1994, abandoned, which is a continuation-in-part of Ser. No. 137,856, Oct. 15, 1993, abandoned.

[51] Int. Cl.$^6$ .................... C07D 401/04; C07D 401/12; A61K 31/44; A61K 31/495
[52] U.S. Cl. .................... 514/254; 514/290; 546/93; 544/361
[58] Field of Search .................... 546/93; 514/290, 514/254; 544/361

[56] References Cited

U.S. PATENT DOCUMENTS

| | | | |
|---|---|---|---|
| 4,282,233 | 8/1981 | Villani | 514/290 |
| 4,826,853 | 5/1989 | Piwinski et al. | 514/290 |
| 4,831,042 | 5/1989 | Villani | 514/316 |
| 4,863,931 | 9/1989 | Schumacher et al. | 514/290 |
| 5,089,496 | 2/1992 | Piwinski et al. | 514/253 |
| 5,104,876 | 4/1992 | Piwinski et al. | 514/254 |
| 5,141,851 | 8/1992 | Brown et al. | 435/15 |
| 5,151,423 | 9/1992 | Piwinski et al. | 514/254 |
| 5,393,890 | 2/1995 | Syoji et al. | 546/80 |

FOREIGN PATENT DOCUMENTS

| | | |
|---|---|---|
| 0 042 544 | 12/1981 | European Pat. Off. |
| 0 270 818 | 6/1988 | European Pat. Off. |
| 0 495 484 A1 | 7/1992 | European Pat. Off. |
| 0 535 730 A2 | 4/1993 | European Pat. Off. |
| WO88/03138 | 5/1988 | WIPO |
| WO89/10363 | 11/1989 | WIPO |
| WO90/13548 | 11/1990 | WIPO |
| WO92/00293 | 1/1992 | WIPO |
| WO92/11034 | 7/1992 | WIPO |
| 94/04561 | 3/1994 | WIPO |
| 94/24107 | 10/1994 | WIPO |

OTHER PUBLICATIONS

Cell, vol. 65, 1–4, Apr. 1991.
The J. of Biological Chemistry, vol. 266, No. 24, pp. 15575–15578, Aug. 25, 1991.
Proc. Natl. Acad. Sci. USA, vol. 87, pp. 3042–3046, Apr. 1990.
Proc. Natl. Acad. Sci. USA, vol. 88, pp. 8631–8635, Oct. 1991.
Nature, vol. 356, pp. 713–715, Apr. 23, 1992.
Proc. Natl. Acad. Sci. USA, vol. 87, pp. 7541–7545, Oct. 1990.
The J. of Biological Chemistry, vol. 265, No. 25, pp. 14701–14704, Sep. 5, 1990.
Proc. Natl. Acad. Sci. USA, vol. 87, pp. 7926–7929, Oct. 1990.
Cell, vol. 62, 81–88, Jul. 13, 1990.
Biochemistry, 31, pp. 3800–3807.
Science, vol. 260, pp. 1934–1937.
Science, vol. 260, pp. 1937–1942.
Reprint of J. Medicinal Chemistry, 34, pp. 457–461, 1991.
Chemical Abstract No. 121: 53129X (1994) for WO 94/04561.
Masci, J. Chem. Soc., Chem. Commun., pp. 1262–1263 (1982).
Masci, J. Org. Chem. 1985, 50, 4081–4087, pp. 4081–4087.
Sebti et al., Proc. Annu. Meeting AM Assoc Cancer Res., 33: A2217 (1992).
Villani et al., Journal of Medical Chemistry, 1972, vol. 15, No. 7 pp. 750–754.
Billah et al., Lipids, vol. 26, No. 12 pp. 1172–1174.
Villani et al., Arzneim.—Forsch/Drug Res. 36 (II), Nr. (1986), pp. 1311–1314.
Chemical Abstracts, vol. 117(21) abst. No. 117:205191–u; Nov. 23, 1992.

Primary Examiner—Alan L. Rotman
Attorney, Agent, or Firm—Henry C. Jeanette

[57] ABSTRACT

A method of inhibiting Ras function and therefore inhibiting cellular growth is disclosed. The method comprises the administration of a compound containing a tricyclic ring system to a biological system. In particular, the method inhibits cellular growth in a mammal such as a human being.

Novel compounds of the formula:

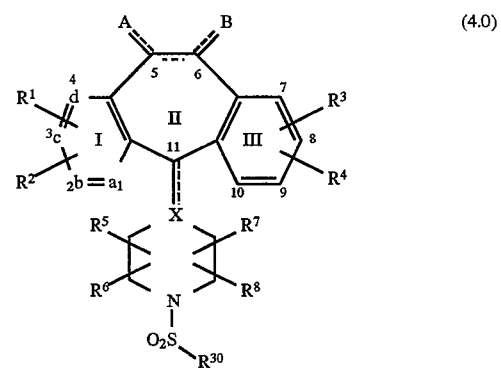

(4.0)

are disclosed.

Also disclosed are processes for making 3-substituted compounds of Formula 4.0.

Further disclosed are novel compounds which are intermediates in the processes for making the 3-substituted compounds of Formula 4.0.

23 Claims, No Drawings

TRICYCLIC SULFONAMIDE COMPOUNDS USEFUL FOR INHIBITION OF G-PROTEIN FUNCTION AND FOR TREATMENT OF PROLIFERATIVE DISEASES

This is a continuation of application Ser. No. 08/312,350, filed Sep. 26, 1994 abandoned, which is a continuation-in-part of application Ser. No. 08/137,856, filed Oct. 15, 1993 (now abandoned).

BACKGROUND

International Publication No. WO92/11034, published Jul. 9, 1992, discloses a method of increasing the sensitivity of a tumor to an antineoplastic agent, which tumor is resistant to the antineoplastic agent, by the concurrent administration of the antineoplastic agent and a potentiating agent of the formula:

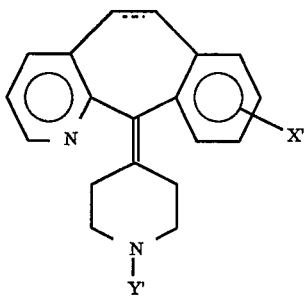

wherein the dotted line represents an optional double bond, X' is hydrogen or halo, and Y' is hydrogen, substituted carboxylate or substituted sulfonyl. For example, Y' can be, amongst others, —COOR' wherein R' is C1 to C6 alkyl or substituted alkyl, phenyl, substituted phenyl, C7 to C12 aralkyl or substituted aralkyl or -2, -3, or -4 piperidyl or N-substituted piperidyl. Y' can also be, amongst others, $SO_2R'$ wherein R' is C1 to C6 alkyl, phenyl, substituted phenyl, C7 to C12 aralkyl or substituted aralkyl. Examples of such potentiating agents include 11-(4-piperidylidene)-5H-benzo[5,6]cyclohepta[1,2-b]pyridines such as Loratadine.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras. One compound disclosed in this invention has been demonstrated to have anti-tumor activity in animal models.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds useful in this invention are represented by Formula 1.0:

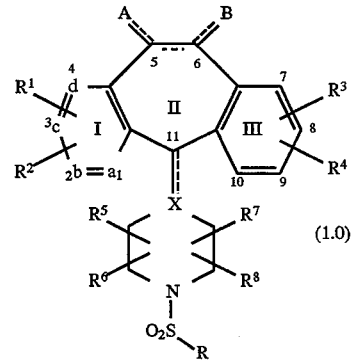

or a pharmaceutically acceptable salt or solvate thereof, wherein:

one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $CR^1$ or $CR^2$;

$R^1$ and $R^2$ are the same or different and each independently represents H, halo, benzotriazol-1yloxy, —$CF_3$, —$OR^{10}$, —$COR^{10}$, —$SR^{10}$, —$S(O)_tR^{11}$ (wherein t is 0, 1 or 2), —$N(R^{10})_2$, —$NO_2$, —$OC(O)R^{10}$, —$CO_2R^{10}$, —$OCO_2R^{11}$, —CN, —$NR^{10}COOR^{11}$, alkynyl, alkenyl or alkyl, which alkyl or alkenyl group may be substituted with halo, —$OR^{10}$ or —$CO_2R^{10}$;

$R^3$ and $R^4$ are the same or different and each independently represents, any of the substituents of $R^1$ and $R^2$, or $R^3$ and $R^4$ together may represent a saturated or unsaturated $C_5$–$C_7$ ring fused to the benzene ring (Ring III);

$R^5$, $R^6$, $R^7$ and $R^9$ each independently represent H, —$CF_3$, —$COR^{10}$, alkyl or aryl, which alkyl or aryl may be substituted with —$OR^{10}$, —$SR^{10}$, $S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or one of $R^5$, $R^6$, $R^7$ and $R^8$ may be taken in combination with R as defined below to represent —$(CH_2)_r$— wherein r is 1 to 4 which may be substituted with lower alkyl, lower alkoxy, —$CF_3$ or aryl;

$R^{10}$ represents H, alkyl or aryl;

$R^{11}$ represents alkyl or aryl;

X represents N or C, which C may contain an optional double bond to carbon atom 11;

the dotted lines represent optional double bonds;

the dotted line between carbon atoms 5 and 6 represents an optional double bond, such that when a double bond is present, A and B independently represent —$R^{10}$, —$OR^{11}$, $OCO_2R^{11}$ or —$OC(O)R^{10}$, and when no double bond is present between carbon atoms 5 and 6, A and B each independently represent $H_2$, —$(OR^{11})_2$, H and halo, dihalo, alkyl and H, (alkyl)$_2$, —H and —$OC(O)R^{10}$, H and —$OR^{10}$, =O, aryl and H, =$NOR^{10}$ or —O—$(CH_2)_p$—O— wherein p is 2, 3 or 4;

R is selected from the group consisting of:

(1) $C_1$ to $C_4$ alkyl (e.g., methyl, ethyl, and butyl);

(2) phenyl substituted with 1 to 3 substituents selected from $R^1$, $R^2$ or $C(O)OR^{20}$, wherein $R^{20}$ is selected from the group consisting of: $C_1$ to $C_6$ alkyl (e.g., methyl) and H;

(3) bridged polycyclic hydrocarbons having from 5 to 10 carbon atoms (e.g., adamantyl, norbornyl, norcamphoryl—i.e., the radical formed from 2-norbornaneone, and 2-norboranol);

(4) substituted bridged polycyclic hydrocarbons, wherein the bridged unsubstituted polycyclic hydrocarbon contains 5 to 10 carbon atoms, wherein the substituents are selected from the group consisting of $C_1$ to $C_6$ alkyl (e.g., methyl), said substituted bridged polycyclic hydrocarbon having from 1 to 8 substituents with two being preferred, and each substituent being the same or different (with the same being preferred);

(5) —$CH_2R^{21}$ wherein $R^{21}$ is aryl (e.g., phenyl or substituted phenyl—i.e., phenyl substituted with 1 to 3, preferably 1, group selected from halo, alkyl, haloalkyl or alkoxy), heteroaryl (e.g., thiophene, thiazole, pyridyl, such as 3- or 4 -pyridyl, or pyridyl N-oxide, such as 3- or 4-pyridyl N-oxide), 2-,3- or 4-piperidyl or N-substituted piperidyl, wherein the substituent on said N-substituted piperidyl is $C_1$ to $C_4$ alkyl, alkylcarbonyl or —$C(O)NH(R^{10})$ wherein $R^{10}$ is H or alkyl, a bridged polycyclic hydrocarbon, or a substituted bridged polycyclic hydrocarbon as described above, e.g.,

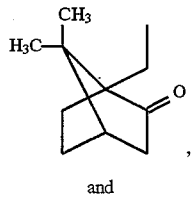

and

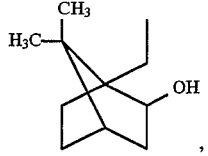

(6) heteroaryl (e.g., thiophene, thiazole, pyridyl, such as 3- or 4- pyridyl, or pyridyl N-oxide, such as 3- or 4-pyridyl N-oxide);

(7) substituted heteroaryl wherein said substituents are selected from the group consisting of: $C_1$ to $C_6$ alkyl (e.g., methyl) and —$NHC(O)R^{22}$ wherein $R^{22}$ is a $C_1$ to $C_6$ alkyl (e.g., methyl), e.g.,

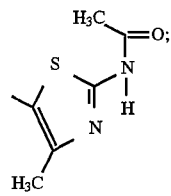

(8) $C_2$ to $C_6$ alkenyl (e.g., —CH=$CH_2$);

(9) benzyl; and

(10) —$N(R^{23})_2$ wherein each $R^{23}$ is independently selected from the group consisting of:$C_1$ to $C_6$ alkyl, H, aryl (e.g., phenyl and substituted phenyl), 2-,3- or 4-piperidyl or N-substituted piperidyl, wherein the substituent on said N-substituted piperidyl is $C_1$ to $C_4$ alkyl, alkylcarbonyl or —$C(O)NH(R^{10})$ wherein $R^{10}$ is H or alkyl (preferably, 3- or 4-N-substituted piperidyl wherein the substituent on the nitrogen is $C_1$ to $C_4$ alkyl, most preferably methyl), heteroaryl (e.g., pyridyl, such as 3- or 4- pyridyl, or 3- or 4-pyridyl N-oxide), preferably, each $R^{23}$ is selected such that there is no more than one H bound to the nitrogen (i.e., preferably there is 0 or 1 H attached to the nitrogen), most preferably one of the two $R^{23}$ substituents is H, more preferably one of the two $R^{23}$ substituents is H and the other $R^{23}$ substituent is other than H.

Those skilled in the art will appreciate that the

moiety can also be represented as

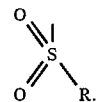

This invention also provides a method for inhibiting tumor growth by administering an effective amount of the tricyclic compounds, described herein, to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, lyn, and fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

This invention provides compounds of formula 4.0:

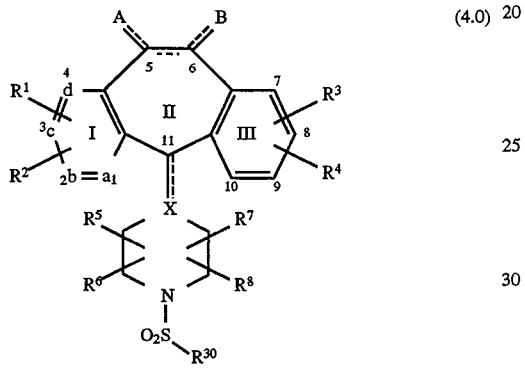

or a pharmaceutically acceptable salt or solvate thereof, wherein:

a, b, c, d, A, B, $R^1$, $R^2$, $R^3$, $R^4$, $R^5$, $R^6$, $R^7$, $R^8$, and X are as defined for formula 1.0; and $R^{30}$ represents:

(1) phenyl substituted with a $C(O)OR^{31}$ group, wherein $R^{31}$ is selected from the group consisting of: $C_1$ to $C_6$ alkyl (e.g., methyl), and H;

(2) bridged polycyclic hydrocarbons having from 5 to 10 carbon atoms (e.g., adamantyl, norbornyl, norcamphoryl—i.e., the radical formed from 2-norbornaneone, and 2-norboranol);

(3) substituted bridged polycyclic hydrocarbons, wherein the bridged unsubstituted polycyclic hydrocarbon contains 5 to 10 carbon atoms, wherein the substituents are selected from the group consisting of $C_1$ to $C_6$ alkyl (e.g., methyl), said substituted bridged polycyclic hydrocarbon having from 1 to 8 substituents with two being preferred, and each substituent being the same or different (with the same being preferred);

(4) —$CH_2R^{32}$ wherein $R^{32}$ is aryl (e.g., phenyl or substituted phenyl—i.e., phenyl substituted with 1 to 3, preferably 1, group selected from halo, alkyl, haloalkyl or alkoxy), heteroaryl (e.g., thiophene, thiazole, pyridyl, such as 3- or 4- pyridyl, or pyridyl N-oxide, such as 3- or 4-pyridyl N-oxide), 2-,3-, or 4-piperidyl or N-substituted piperidyl, wherein the substituent on said N-substituted piperidyl is $C_1$ to $C_4$ alkyl, alkylcarbonyl or —$C(O)NH(R^{10})$ wherein $R^{10}$ is H or alkyl, a bridged polycyclic hydrocarbon, or a substituted bridged polycyclic hydrocarbon as described above, e.g.,

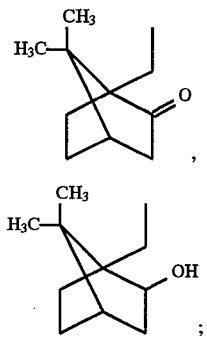

(5) heteroaryl (e.g., thiophene, thiazole, pyridyl, such as 3- or 4- pyridyl, or pyridyl N-oxide, such as 3- or 4-pyridyl N-oxide);

(6) substituted heteroaryl wherein said substituents are selected from the group consisting of: $C_1$ to $C_6$ alkyl (e.g., methyl) and —$NHC(O)R^{22}$ wherein $R^{22}$ is a $C_1$ to $C_6$ alkyl (e.g., methyl), e.g.,

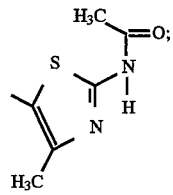

(7) $C_2$ to $C_6$ alkenyl (e.g., —CH=$CH_2$); and (8) —$N(R^{40})_2$ wherein each $R^{40}$ is independently selected from the group consisting of: H, aryl (e.g., phenyl and substituted phenyl), 2-,3- or 4-piperidyl or N-substituted piperidyl, wherein the substituent on said N-substituted piperidyl is $C_1$ to $C_4$ alkyl, alkylcarbonyl or —$C(O)NH(R^{10})$ wherein $R^{10}$ is H or alkyl, and heteroaryl (e.g., pyridyl, such as 3- or 4-pyridyl, or 3- or 4- pyridyl N-oxide), preferably, each $R^{40}$ is selected such that there is no more than one H bound to the nitrogen (i.e., preferably there is 0 or 1 H attached to the nitrogen), most preferably one of the two $R^{40}$ substituents is H, more preferably one of the two $R^{40}$ substituents is H and the other $R^{40}$ substituent is other than H.; and with the proviso that when R represents —$CH_2R^{32}$ wherein $R^{32}$ is aryl, and when $R^1$ and $R^2$ are H, then $R^4$ is Cl at the C-8 position.

The tricyclic compounds useful in the methods of this invention inhibit cellular growth. Without wishing to be bound by theory, it is believed that these compounds may function through the inhibition of G-protein function, such as ms p21 isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

The tricyclic compounds useful in the methods of this invention are described in: (1) U.S. Pat. No. 4,282,233, the disclosure of which is incorporated herein by reference thereto.

This invention also provides a process for producing 3-nitro substituted compounds. The process comprises reacting one molar equivalent of a compound:

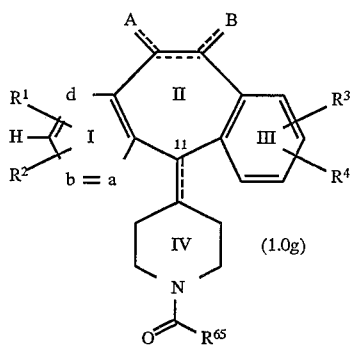

(1.0g)

wherein $R^1$, $R^2$, $R^3$, $R^4$, A, B, a, b, d, and the dotted lines are as defined for Formula 1.0; and $R^{65}$ represents H or —$OR^{66}$ wherein $R^{66}$ represents alkyl (e.g., $C_1$ to $C_4$ alkyl, preferably ethyl); with one molar equivalent of a nitrating reagent, said nitrating reagent being preformed (i.e., prepared first) by mixing, at cold temperature (e.g., at 0° C.) equimolar amounts of tetrabutyl ammonium nitrate with trifluoroacetic anhydride; the reaction of the nitrating reagent with the compound of Formula 1.0g taking place in a suitable aprotic solvent (e.g., methylene chloride, chloroform, toluene or tetrahydrofuran); said reaction with said nitrating reagent being conducted at a temperature and for a period of time sufficient to allow the reaction to proceed at a reasonable rate to produce the desired final 3-nitro compound of Formula 1.0h (described below)—i.e., the reaction of the compound of Formula 1.0g with said nitrating reagent is conducted at an intial temperature of 0° C., and said reaction temperature is thereafter allowed to rise to about 25° C. during the reaction time period. The reaction usually proceeds overnight to completion, i.e., the reaction usually proceeds for about 16 hours. The reaction can be conducted within a temperature of 0° C. to about 25° C. during a time period of about 10 to about 24 hours. Preferably the reaction is initially conducted at 0° C. and the temperature is allowed to warm up to 25° C. The reaction produces the 3-nitro compound:

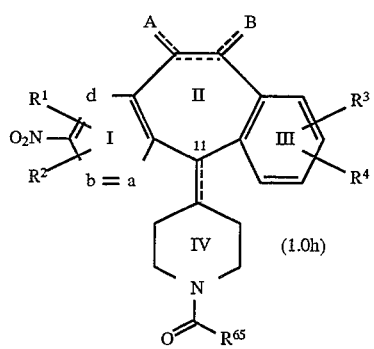

(1.0h)

is produced.

The compound of Formula 1.0h can then be converted to other 3-substituted products by methods well known to those skilled in the art. For example, the 3-nitro compounds can be converted to 3-amino, 3-halo, 3-cyano, 3-alkyl, 3-aryl, 3-thio, 3-arylalkyl, 3-hydroxyl, and 3-$OR^{67}$ wherein $R^{67}$ is alkyl or aryl. The 3-substituted compounds can then be converted to final products by the procedures described herein.

This invention also provides a process for producing 3-nitro compounds of the formula:

by producing a compound of Formula 1.0h from 1.0g as described above; and then hydrolyzing the compound of Formula 1.0h by dissolving the compound of Formula 1.0h in a sufficient amount of concentrated acid (e.g., concentrated HCl or aqueous sulfuric acid), and heating the resulting mixture to a temperature sufficient to remove (hydrolyze) the —$C(O)R^{65}$ substituent, for example, heating to reflux or to a temperature of about 100° C. This hydrolysis process is exemplified in Preparative Example 28.

The compound of Formula 1.0i can then be converted to other 3-substituted compounds as discussed above for the compounds of Formula 1.0h. The compounds of Formula 1.0i can then be converted to compounds of this invention by the methods described herein.

This invention also provides a process for producing compounds of the formula:

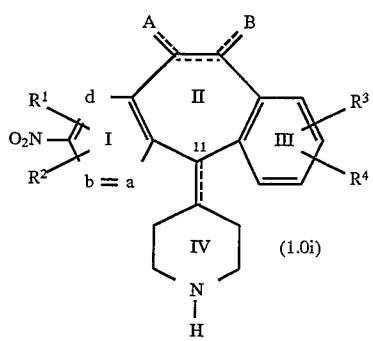

(1.0i)

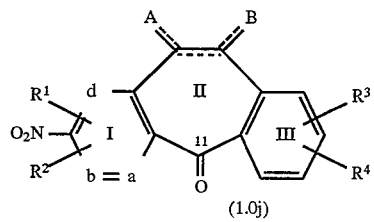

(1.0j)

by reacting one molar equivalent a compound of formula:

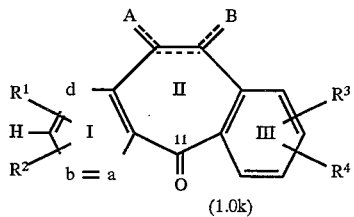

(1.0k)

with one molar equivalent of a nitrating reagent, said nitrating reagent being preformed (i.e., prepared first) by mixing, at cold temperature (e.g., at 0° C.) equimolar amounts of tetrabutyl ammonium nitrate with trifluoroacetic anhydride; the reaction of the nitrating reagent with the compound of Formula 1.0k taking place in a suitable aprotic solvent (e.g., methylene chloride, chloroform, toluene or tetrahydrofuran); said reaction with said nitrating reagent being conducted at a temperature and for a period of time sufficient to allow the reaction to proceed at a reasonable rate to produce the desired final 3-nitro compound of Formula 1.0j—i.e., the reaction of the compound of Formula 1.0k with said nitrating reagent is conducted at an intial temperature of 0° C., and said reaction temperature is thereafter allowed to rise to about 25° C. during the reaction time period. The reaction usually proceeds overnight to completion, i.e., the reaction usually proceeds for about 16 hours. The reaction can be conducted within a temperature of 0° C. to about 25° C. during a time period of about 10 to about 24 hours. Preferably the reaction is initially conducted at 0° C. and the temperature is allowed to warm up to 25° C. In Formulas 1.0j and 1.0k, $R^1$, $R^2$, $R^3$, $R^4$, A, B, a, b, d, and the dotted lines are as defined for Formula 1.0

The compounds of Formula 1.0j can be converted to compounds of Formula 1.0h by methods described below. Also, as discussed above for the compounds of Formula 1.0h, the compounds of Formula 1.0j can be converted to other 3-substituted compounds wherein the substituents are those discussed above for Formula 1.0h.

The compounds of Formula 1.0j can be converted to compounds of Formula 1.0m:

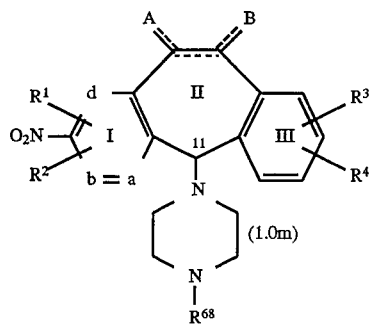

(1.0m)

wherein $R^{68}$ is H or —COOR$^a$ wherein $R^a$ is a $C_1$ to $C_3$ alkyl group (preferably $R^{68}$ is H), by reducing a compound of Formula 1.0j with a suitable reducing agent (such as sodium borohydride) in a suitable solvent (such as ethanol or methanol) at a suitable temperature to allow the reaction to proceed at a reasonable rate (e.g., 0° to about 25° C.); reacting the resulting product (Formula 1.0j wherein the =O has been reduced to a —OH) with a chlorinating agent (e.g., thionyl chloride) in an suitable organic solvent (e.g., benzene, toluene or pyridine) at a suitable temperature to allow the reaction to proceed at a reasonable rate (e.g., about –20° to about 20° C., preferably at –15° C.) to produce a compound of Formula 1.0n:

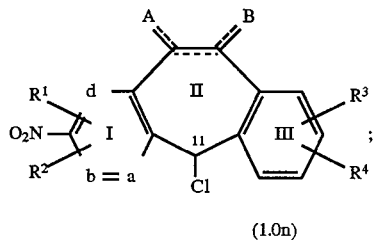

(1.0n)

and reacting a compound of Formula 1.0n with a compound of the formula:

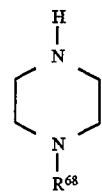

wherein $R^{68}$ is as previously defined, and is preferably H, in a suitable organic solvent (such as tetrahydrofuran or toluene) containing a suitable base (such as triethylamine or N-methylmorpholine) at a suitable temperature to allow the reaction to proceed at a reasonable rate (e.g., 25° to about 120° C.).

Compounds of Formula 1.0m can be converted to compounds of this invention by the methods disclosed herein. Also, as discussed above for the compounds of Formula 1.0h, the compounds of Formula 1.0m can be converted to other 3-substituted compounds wherein the substituents are those discussed above for Formula 1.0h.

This invention also provides novel compounds (produced in the above described processes as intermediates to the compounds of this invention) having the formulas:

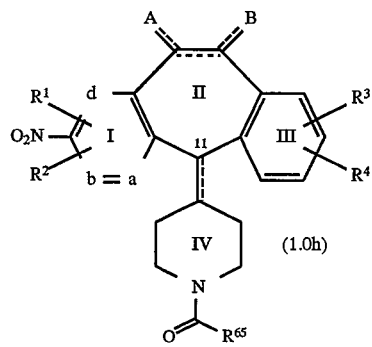

(1.0h)

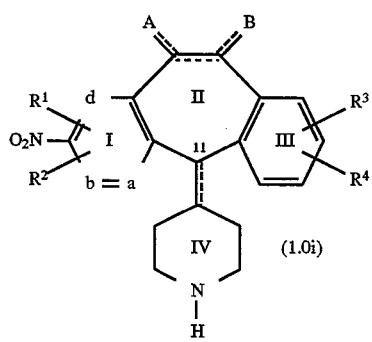

(1.0i)

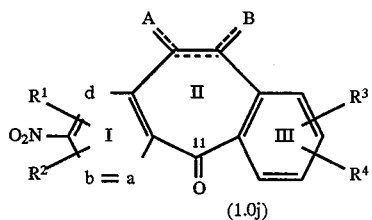

(1.0j)

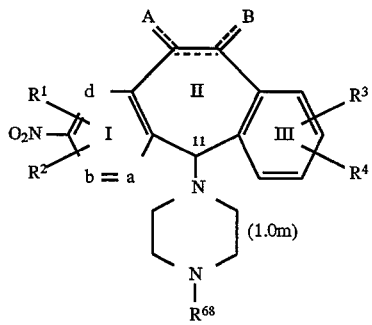

(1.0m)

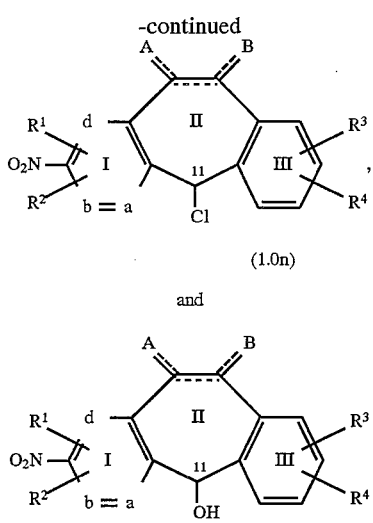

wherein all substituents are as defined herein.

Preferably, for the intermediate compounds of the processes of this invention, $R^1$ and $R^2$ are H; $R^3$ is halo, most preferably Cl, in the C-8 position; $R^4$ is H; and A and B are H when the double between C-5 and C-6 is present, and A and B are $H_2$ when the bond between C-5 and C-6 is a single bond (most preferably the bond between C-5 and C-6 is a single bond). Those skilled in the art will appreciate that Rings I, II, and/or III can be further substituted, as described herein, to produce the desired compounds of the invention.

Examples of such novel intermediate compounds include:

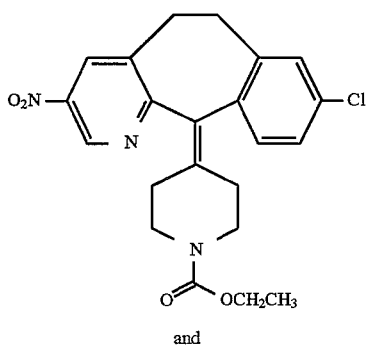

and

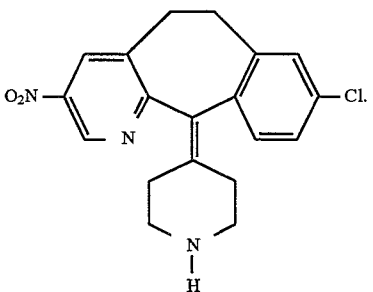

DETAILED DESCRIPTION OF THE INVENTION

As used herein, the following terms are used as defined below unless otherwise indicated:

$M^+$-represents the molecular ion of the molecule in the mass spectrum;

$MH^+$-represents the molecular ion plus hydrogen of the molecule in the mass spectrum;

alkyl—(including the alkyl portions of alkoxy, alkylamino and dialkylamino)-represents straight and branched carbon chains and contains from one to twenty carbon atoms, preferably one to six carbon atoms;

alkanediyl-represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, —$CH_2CH_2CH_2$—, —$CH_2CHCH_3$, —$CHCH_2CH_3$, etc.

alkenyl-represents straight and branched carbon chains having at least one carbon to carbon double bond and containing from 2 to 12 carbon atoms, preferably from 2 to 6 carbon atoms;

alkynyl-represents straight and branched carbon chains having at least one carbon to carbon triple bond and containing from 2 to 12 carbon atoms, preferably from 2 to 6 carbon atoms;

aryl (including the aryl portion of aryloxy)-represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted with one or more of halo, alkyl, hydroxy, alkoxy, phenoxy, $CF_3$, amino, alkylamino, dialkylamino, —$COOR^{10}$ or —$NO_2$;

cycloalkyl-represents saturated carbocyclic rings branched or unbranched of from 3 to 20 carbon atoms, preferably 3 to 7 carbon atoms;

halo-represents fluoro, chloro, bromo and iodo;

heterocycloalkyl-represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —$NR^{10}$— (suitable heterocycloalkyl groups including 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.);

heteroaryl-represents cyclic groups, optionally substituted with $R^3$ and $R^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., 2-, 3- or 4-pyridyl (optionally substituted with $R^3$ and $R^4$), pyridyl N-oxide:

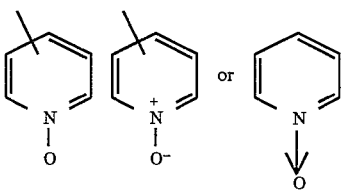

(e.g., 2-, 3- or 4-pyridyl N-oxide, optionally substituted with $R^3$ and $R^4$); and lower alkyl-represents straight and branched carbon chains and contains from one to five carbon atoms;

Reference to the positions of the substituents in Rings I and III, for example, is based on the numbered ring structure:

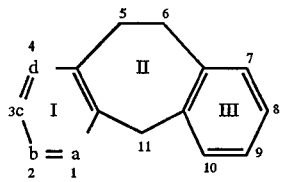

For example, in Formula 1.0, $R^1$ can be at the C-3 position and $R^2$ can be at the C-4 or C-2 position. Also, for example, $R^4$ can be at the C-8 position and $R^3$ can be at the C-9 position.

Lines drown into the ring systems indicate that the indicted bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemi-hydrate. In general, the solvated forms, with pharmaceutically acceptable solvents such as water, ethanol and the like am equivalent to the unsolvated forms for purposes of the invention.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated am salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of formula 1.0 include compounds of formulas 1.1 to

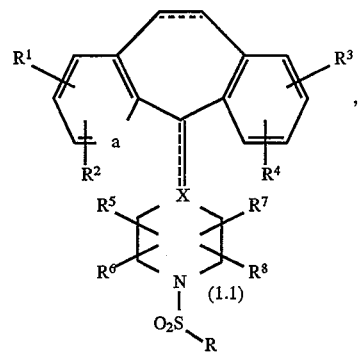

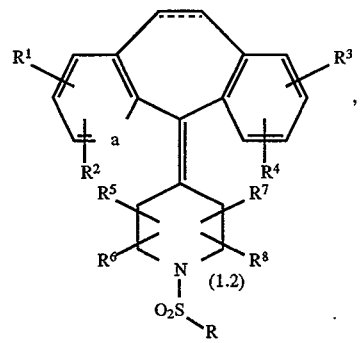

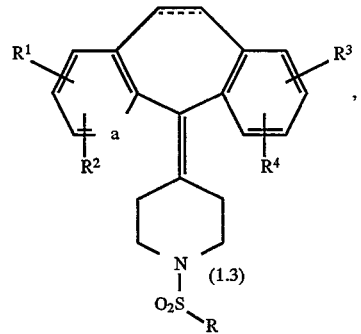

and

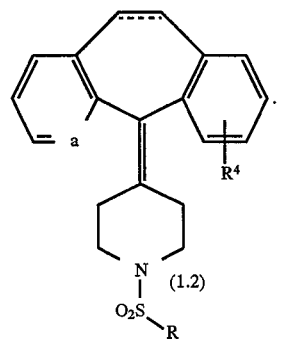

wherein the substituents are as defined above.

Compounds of formula 1.0 include compounds wherein the nitrogen is located at position "a"; $R^5$, $R^6$, $R^7$, and $R^8$ are H; A and B are both $H_2$; X is carbon; the bond between positions 5 and 6 is a single bond; and the bond between the piperidyl ring and the cycloheptyl ring is a double bond— i.e., the bond between C-11 and X is a double bond.

Compounds of formula 1.0 also include compounds wherein b, c and d are C; a is N; $R^1$ and $R^2$ each independently represent H, benzotriazol-1yloxy, $C_1$ to $C_4$ alkyl (e.g., $CH_3$) or halo (preferably, $R^1$ is halo or $C_1$ to $C_4$ at the C-3 position and $R^2$ is at the C-4 position wherein $R^2$ is H, benzotriazol-1yloxy or halo, most preferably $R^1$ is halo or $C_1$ to $C_4$ alkyl at the C-3 position and $R^2$ is halo at the C-4 position); $R^3$ and $R^4$ are independently H or halo (preferably, $R^4$ is halo at the C-8 position and $R^3$ is H, most preferably $R^4$ is Cl at the C-8 postion); the dotted lines between positions 5 and 6 are absent (i.e., there is a single bond between C-5 and C-6) and A and B are both $H_2$ or the dotted line between positions 5 and 6 is present (i.e., there is a double bond between (C-5 and C-6) and A and B are both H; $R^5$, $R^6$, $R^7$, and $R^8$ each represent H; X represents C and the dotted line drawn to X represents a double bond or X represents C or N and the dotted line is absent—i.e., there is a single bond between C-11 and the carbon or nitrogen; and R represents $—CH_2R^{21}$ wherein $R^{21}$ is aryl (e.g., phenyl or substituted phenyl—i.e., phenyl substituted with 1 to 3, preferably 1, group selected from halo, alkyl, haloalkyl or alkoxy), heteroaryl (e.g., thiophene, thiazole, pyridyl, such as 3- or 4- pyridyl, or pyridyl N-oxide, such as 3- or 4-pyridyl N-oxide), 2-,3-, or 4-piperidyl or N-substituted piperidyl, wherein the substituent on said N-substituted piperidyl is $C_1$ to $C_4$ alkyl, alkylcarbonyl or $—C(O)NH(R^{10})$ wherein $R^{10}$ is H or alkyl (preferably 3- or 4-N-substituted piperidyl wherein said substitutent on the nitrogen is $C_1$ to $C_4$ alkyl, more preferably methyl);.

Preferred compounds useful in this invention are represented by formula 1.5:

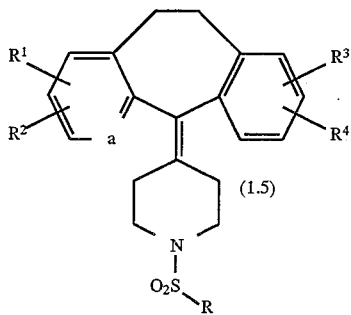

(1.5)

wherein the substutuents are as defined above.

Compounds of formula 1.0 useful in this invention are represented by formula 2.0:

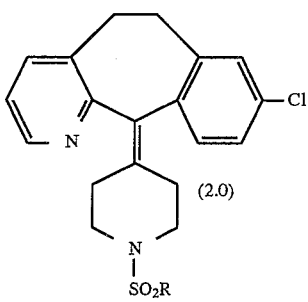

(2.0)

wherein R is as defined above.

Examples of compounds useful in this invention include but are not limited to:

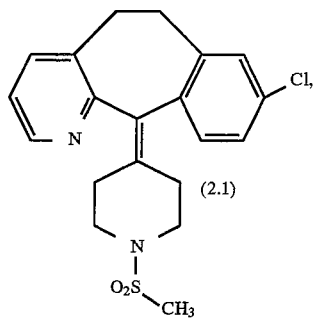

(2.1)

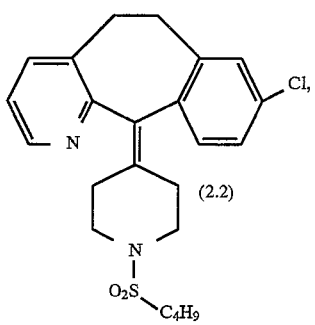

(2.2)

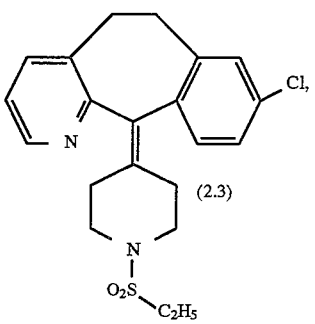

(2.3)

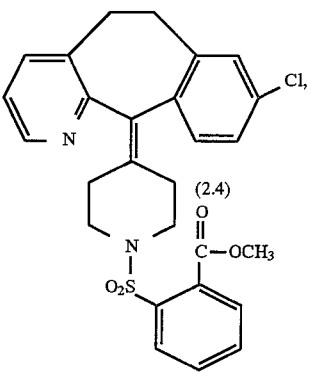

(2.4)

-continued
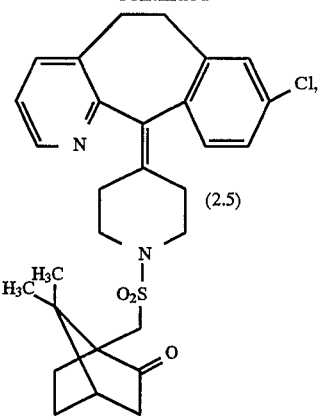
(2.5)
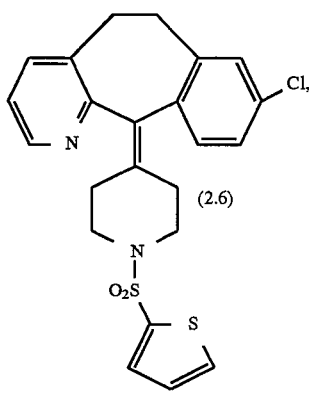
(2.6)
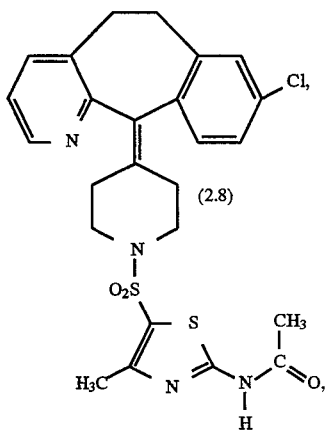
(2.8)
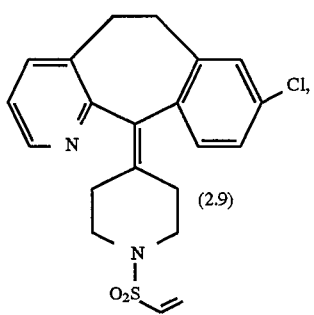
(2.9)
-continued
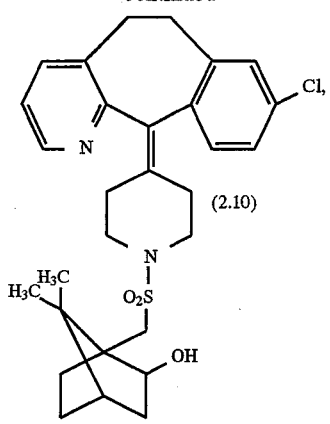
(2.10)
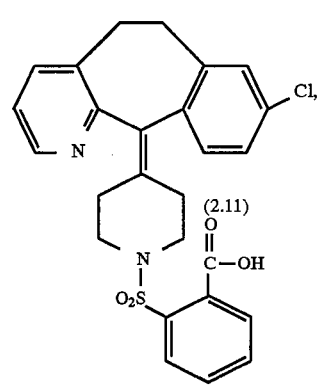
(2.11)
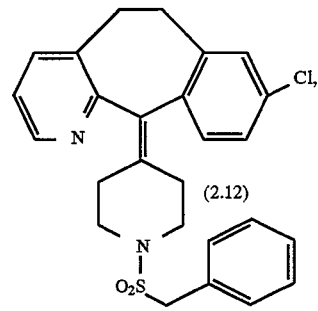
(2.12)
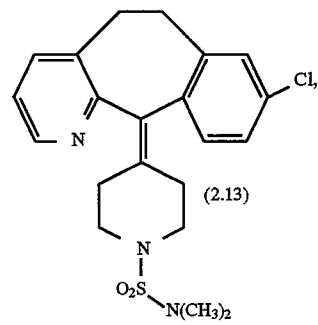
(2.13)
and

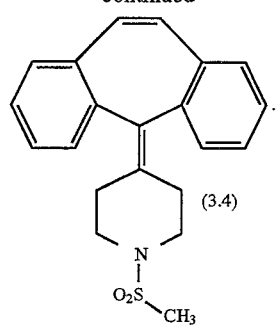
(3.4)
Compounds of formula 4.0 include:
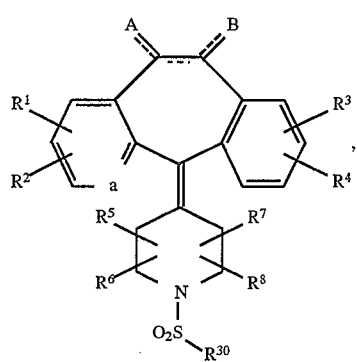
(4.0A)
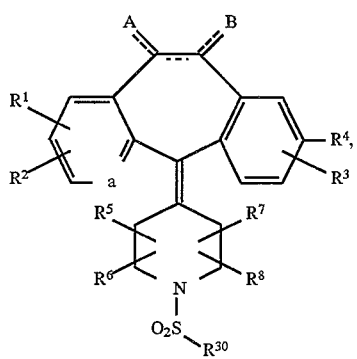
(4.0B)
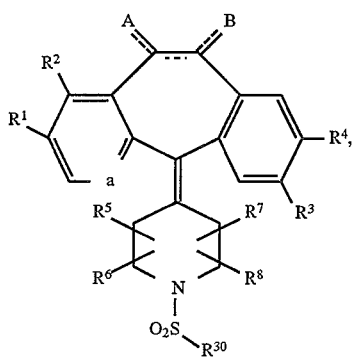
(4.0C)
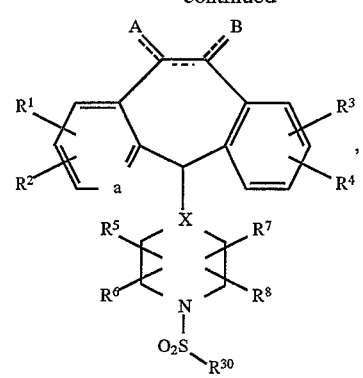
(4.0D)
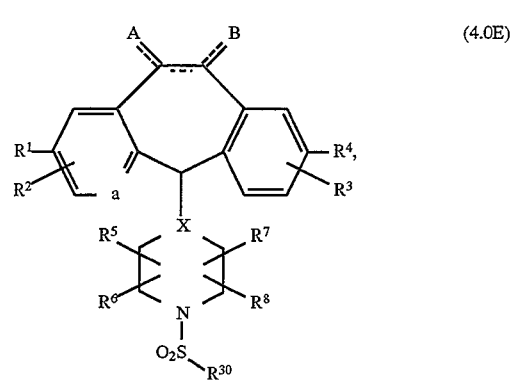
(4.0E)
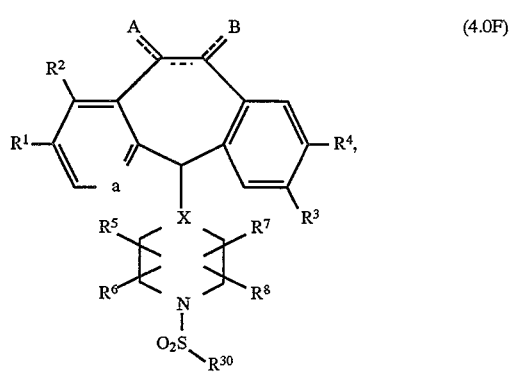
(4.0F)
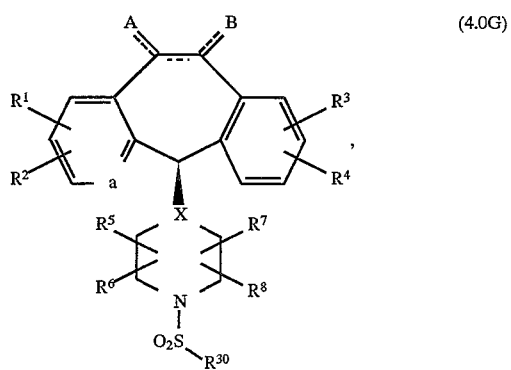
(4.0G)

(4.0H)

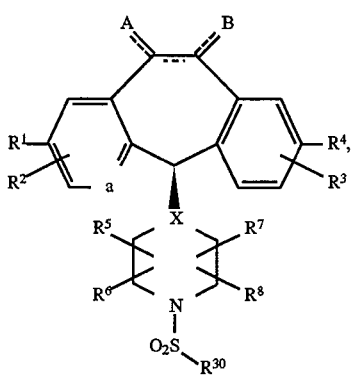

(4.0I)

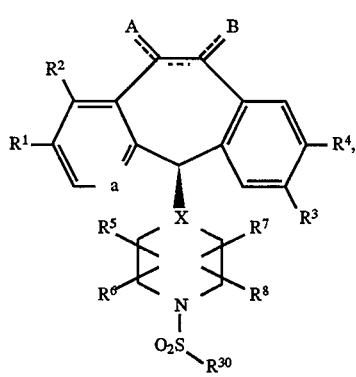

(4.0J)

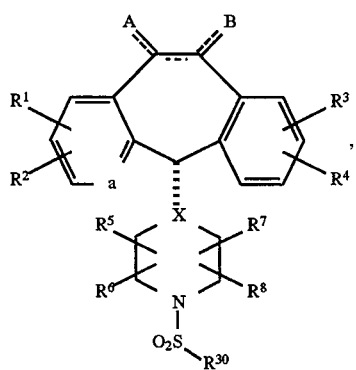

(4.0K)

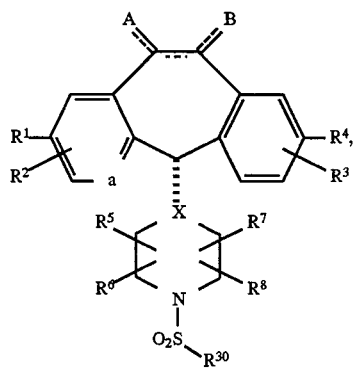

and (4.0L)

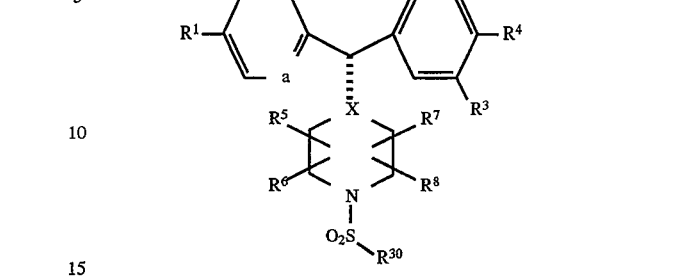

wherein $R^1$, $R^2$, $R^3$, $R^4$, $R^5$, $R^6$, $R^7$, $R^8$, $R^{30}$, X, a, A, and B are as defined above for formula 4.0.

Preferably, for compounds of formula 4.0, a is N;. $R^1$ and $R^2$ are each independently selected from H, benzotriazol-1yloxy, $C_1$ to $C_4$ alkyl or halo, most preferably $R^1$ is halo (e.g., Cl or Br) or $C_1$ to $C_4$ alkyl (more preferably methyl) at the C-3 position and $R^2$ is at the C-4 position, more preferably $R^1$ is halo (e.g., Cl or Br) or $C_1$ to $C_4$ alkyl (more preferably methyl) at the C-3 position and $R^2$ is halo (e.g., Cl or Br) at the C-4 position; $R^3$ and $R^4$ are each independently selected from H or halo, most preferably $R^3$ is H and $R^4$ is halo, more preferably $R^3$ is H and $R^4$ is halo at the C-8 position, and even more preferably $R^3$ is H and $R^4$ is Cl at the C-8 position; $R^5$, $R^6$, $R^7$, and $R^8$ are each H; A and B are each H when the double bond is present between C-5 and C-6; A and B are each $H_2$ when the bond between C-5 and C-6 is a single bond; and $R^{30}$ represents —$CH_2R^{32}$ wherein $R^{32}$ is aryl (e.g., phenyl or substituted phenyl—i.e., phenyl substituted with 1 to 3, preferably 1, group selected from halo, alkyl, haloalkyl or alkoxy), heteroaryl (e.g., thiophene, thiazole, pyridyl, such as 3- or 4- pyridyl, or pyridyl N-oxide, such as 3- or 4-pyridyl N-oxide), 3-, or 4-piperidyl or N-substituted piperidyl, wherein the substituent on said N-substituted piperidyl is $C_1$ to $C_4$ alkyl, alkylcarbonyl or —C(O)NH($R^{10}$) wherein $R^{10}$ is H or alkyl (preferably 3- or 4-N-substituted piperidyl wherein said substitutent on the nitrogen is $C_1$ to $C_4$ alkyl, more preferably methyl), most preferably $R^{32}$ represents 3- or 4- pyridyl, 3- or 4- pyridyl N-oxide, or 3- or 4-N-substituted piperidyl, wherein the substituent on the nitrogen of said N-substituted piperidyl is $C_1$ to $C_4$ alkyl (more preferably methyl).

Compounds of formula 4.0 also include:

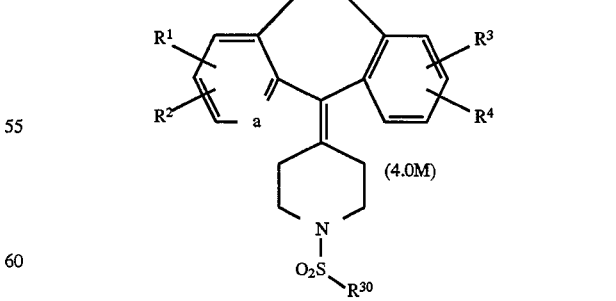

(4.0M)

and

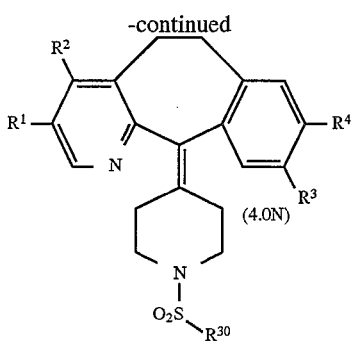
(4.0N)
wherein the substituent groups are as defined above.
Compounds of formula 4.0 further include:
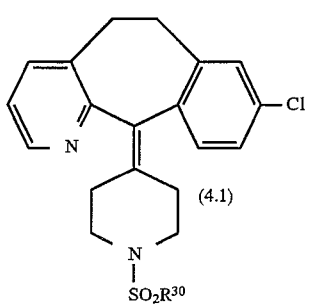
(4.1)
wherein $R^{30}$ is as defined above.
Examples of compounds of formula 4.1 include but are not limited to:
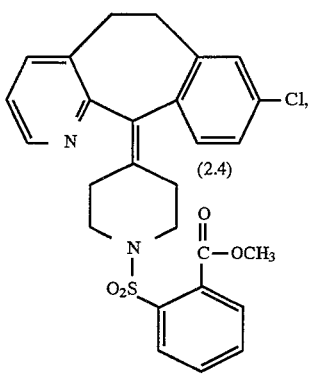
(2.4)
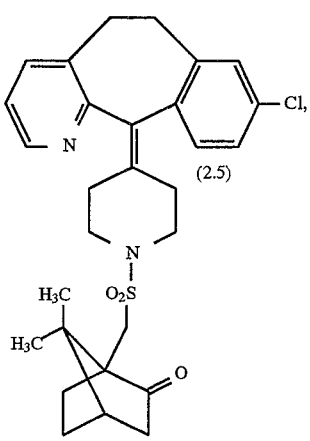
(2.5)
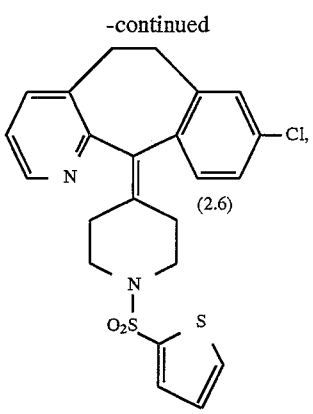
(2.6)
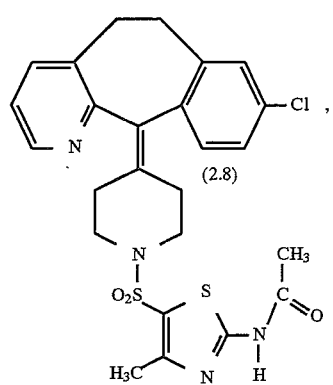
(2.8)
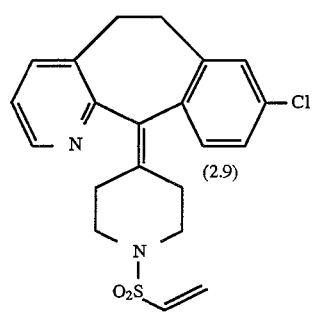
(2.9)
and
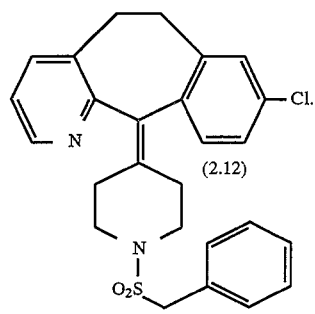
(2.12)

This invention also provides the compounds:

(2.2)

(2.3)

and

Compounds of the invention also include the compounds:

(8.0)

(8.1)

(8.2)

(8.3)

(8.4)

(8.5)

(8.6)

27
-continued

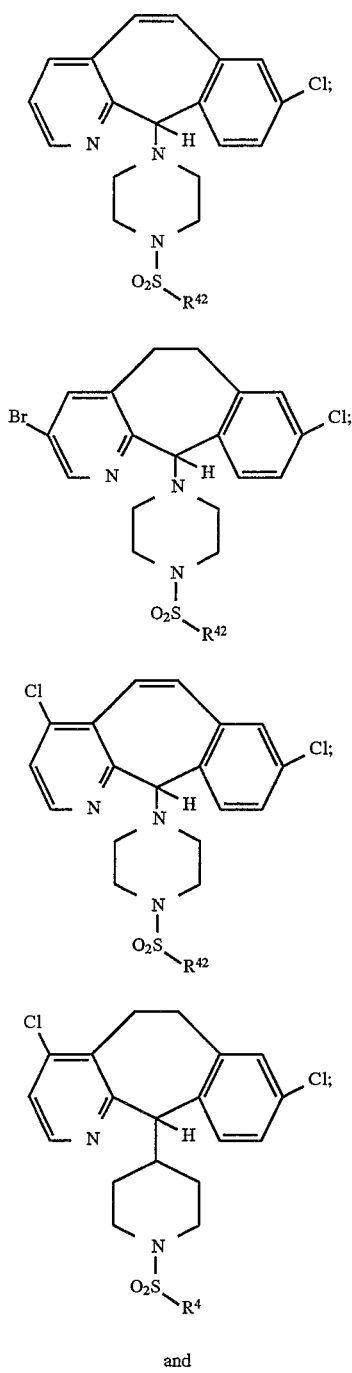

(8.11)

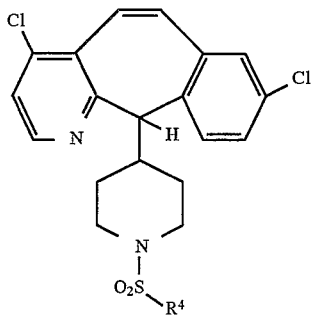

and wherein R⁴² is selected from:

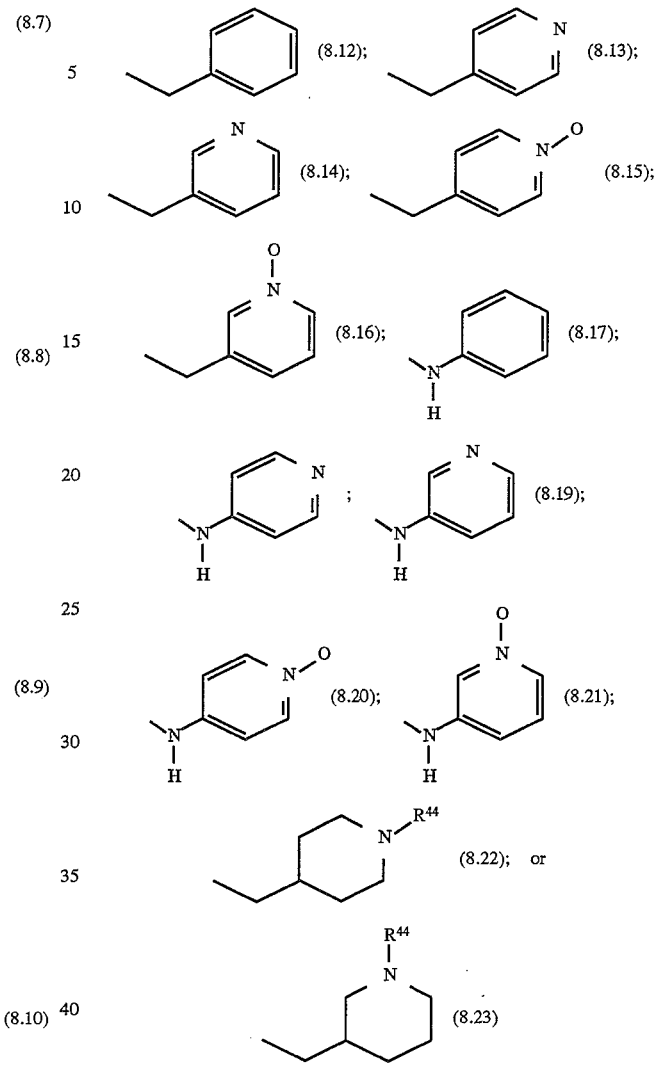

wherein R⁴⁴ is selected from H, alkyl (e.g., methyl), alkylcarbonyl (e.g., CH₃C(O)—), alkoxycarbonyl (e.g., CH₃OC(O)—) or —C(O)NHR¹⁰ wherein R¹⁰ is H or alkyl, most preferably R⁴⁴ is alkyl, and more preferably R⁴⁴ is methyl.

The following processes may be employed to produce compounds of Formula 400.00.

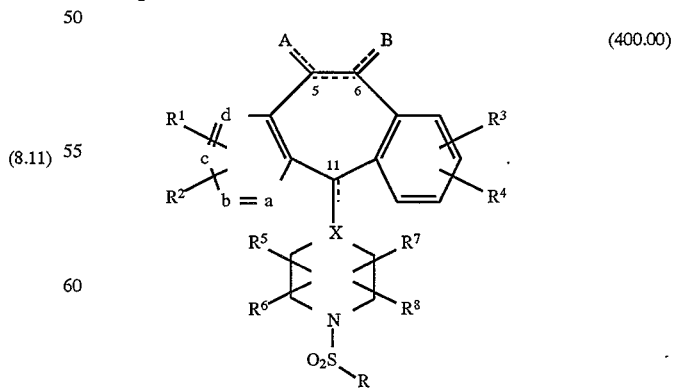

Those skilled in the art will appreciate that the processes described for making compounds of formula 400.00 are applicable to the compounds of formula 1.0 and 4.0.

A. A compound of Formula 405.00 may be reacted with a compound of Formula 410.00 in the presence of base to produce compounds of Formula 400.00:

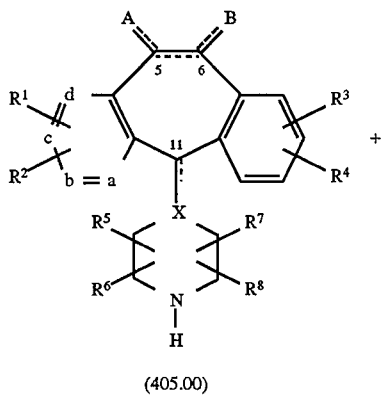

(405.00)

(410.00)

Representative examples of appropriate bases are pyridine and triethylamine, or inorganic bases such as sodium carbonate. Compound 410.00, shown above as a sulfonyl chloride, may also be a sulfonyl halide or a sulfonic anhydride (R—SO$_2$OSO$_2$R).

The compound of Formula 410.00, wherein R is R$^{42}$, wherein R$^{42}$ represents 8.13, 8.14, 8.22, or 8.23, could be prepared by conveying the alcohol, R$^{42}$OH, to the mesylate, R$^{42}$OSO$_2$CH$_3$, with one molar equivalent of methanesulfonyl chloride in the presence of a base (such as pyridine or triethylamine) in a solvent (such as methylene chloride or chloroform) at temperature of 0° to 25° C. The mesylate could be converted to the thiol, R$^{42}$SH, by reacting the mesylate with NaSH in a solvent (such as methanol or ethanol) at a temperature of 0° to 50° C. The thiol could be oxidized to the sulfonic acid, R$^{42}$SO$_3$H, by oxidizing agents (such as KMnO$_4$, or H$_2$O$_2$ in acetic acid). The sulfonic acid could be converted to the sulfonyl chloride, R$^{42}$SO$_2$Cl, by reacting the sulfonic acid with PCl$_5$.

The compound of Formula 410.00, wherein R is R$^{42}$, wherein R$^{42}$ represents 8.18 or 8.19, could be prepared by reacting the amine, R$^{42}$NH$_2$, with SO$_2$Cl$_2$ in the presence of a base (such as pyridine or triethylamine) in a solvent (such as methylene chloride or chloroform) at temperature of 0° to 25° C.

Compounds of Formula 405.00 may be prepared by cleaving the group COOR$^a$ from the corresponding carbamates 415.00, for example, via acid hydrolysis (e.g., HCl) or base hydrolysis (e.g., KOH):

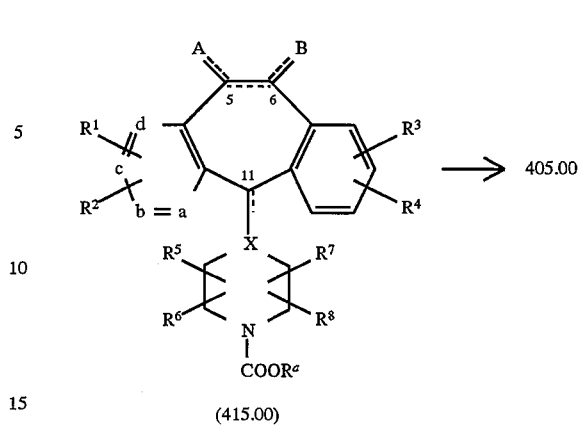

(415.00)

wherein R$^a$ is a group which does not prevent the cleavage reaction, e.g., R$^a$ is an optionally substituted alkyl such as ethyl.

Alternatively, depending upon the nature of R$^a$, as determined by one skilled in the art, Compound 415.00 may be treated with an organometallic reagent (e.g., CH$_3$Li), a reductive reagent (e.g., Zn in acid), etc., to form compounds of Formula 405.00.

Compound 415.00 may be prepared from the N-alkyl compound shown as Formula 420.00 below, in the manner disclosed in U.S. Pat. Nos. 4,282,233 and 4,335,036.

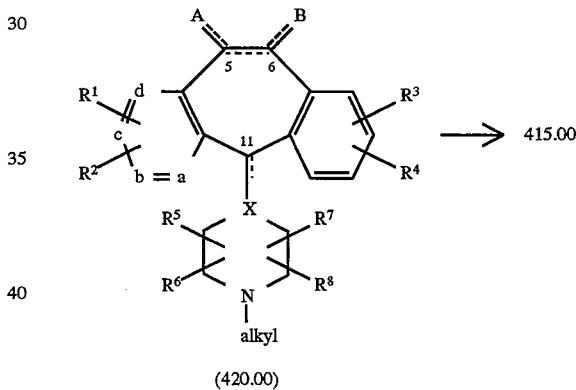

(420.00)

It also will be apparent to one skilled in the art that there are other methods for converting Compound 420.00 to Compound 405.00. For example, treatment of Compound 420.00 with BrCN via von Braun reaction conditions would provide nitrile 420.00a. Subsequent hydrolysis of the nitrile under either aqueous basic or acidic conditions would produce Compound 405.00. This method is preferable when there is substitution on the piperidine or piperazine ring.

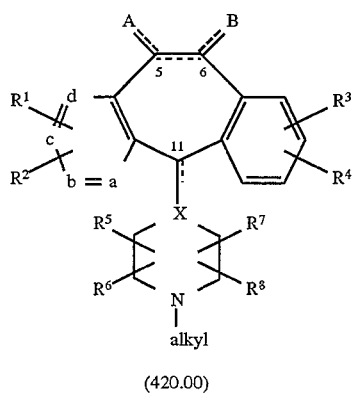

(420.00)

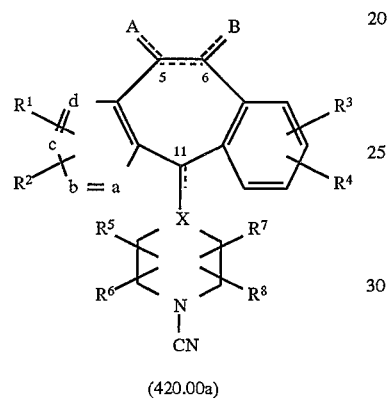

(420.00a)

PREPARATION OF SINGLE BOND COMPOUNDS

Compounds of Formula 400.00, wherein X is carbon and the bond to carbon 11 (C-11) is a single bond, can be prepared by reducing compounds of Formula 405.00, wherein X is carbon and the bond to C-11 is a double bond, with lithium aluminum hydride in tetrahydrofuran. Conversion to final products can be done following the process described above for conversion of compounds of Formula 405.00 to compounds of Formula 400.00.

PREPARATION OF DOUBLE BOND COMPOUNDS

Compounds of Formula 400.00, wherein X is a carbon atom having an exocyclic double bond to carbon 11, may be prepared from compound 420.00 as described above. Compounds of Formula 420.00 may be produced by the methods disclosed generally in U.S. Pat. No. 3,326,924 or alternatively may be prepared by a ring closure reaction, wherein the desired cycloheptene ring is formed by treating compound 425.00 with a super acid. Suitable super acids for this purpose include, for example, HF/BF$_3$, CF$_3$SO$_3$H (triflic acid), CH$_3$SO$_3$H/BF$_3$, etc. The reaction can be performed in the absence of, or with, an inert co-solvent such as CH$_2$Cl$_2$. The temperature and time of the reaction vary with the acid employed. For example, with HF/BF$_3$ as the super acid system the temperature may be controlled so as to minimize side reactions, such as HF addition to the exocyclic double bond. For this purpose, the temperature is generally in the range of from about +5° C. to −50° C. With CF$_3$SO$_3$H as the super acid system, the reaction may be run at elevated temperatures, e.g., from about 25° C. to about 150° C. and at lower temperatures but the reaction then takes longer to complete.

Generally the super acid is employed in excess, preferably in amounts of from about 1.5 to about 30 equivalents.

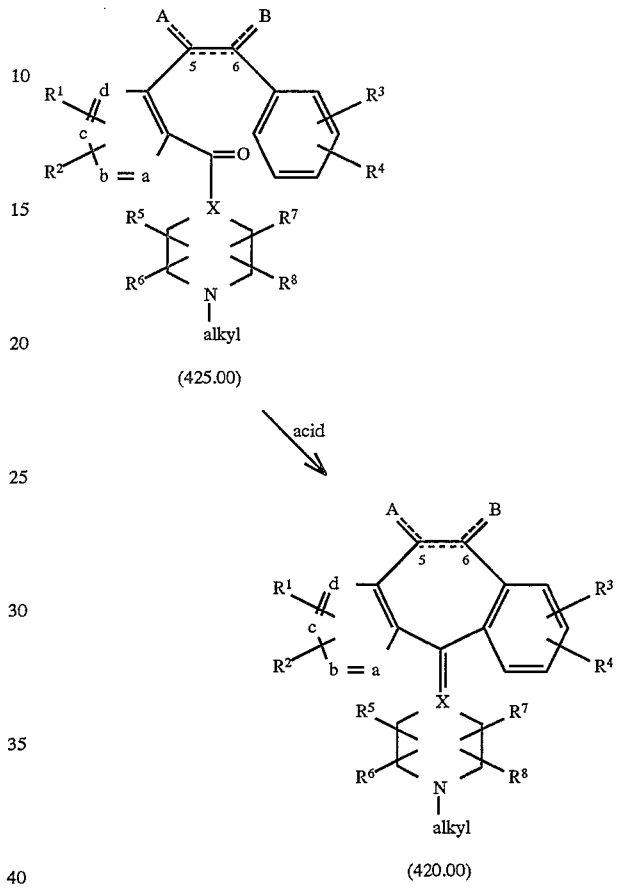

A ketone compound of Formula 425.00 may be formed by hydrolysis of 430.00, e.g., such as by reacting a Grignard intermediate of Formula 430.00 with an aqueous acid (e.g., aqueous HCl). I$^a$ in Formula 430.00 represents chloro, bromo or iodo.

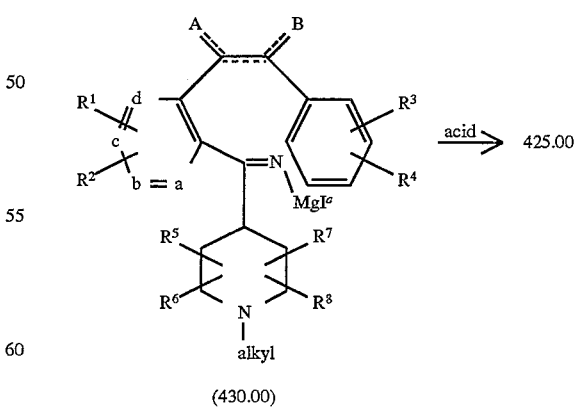

The Grignard intermediate 430.00 is formed by the reaction of the cyano compound 435.00 with an appropriate Grignard reagent 440.00 prepared from 1-alkyl-4halopiperidine. The reaction is generally performed in an inert solvent, such as ether, toluene, or tetrahydrofuran, under general Grignard conditions e.g., temperature of from about 0° C. to about 75° C. Alternatively, other organometallic derivatives of the 1alkyl-4-halo piperidine can be employed.

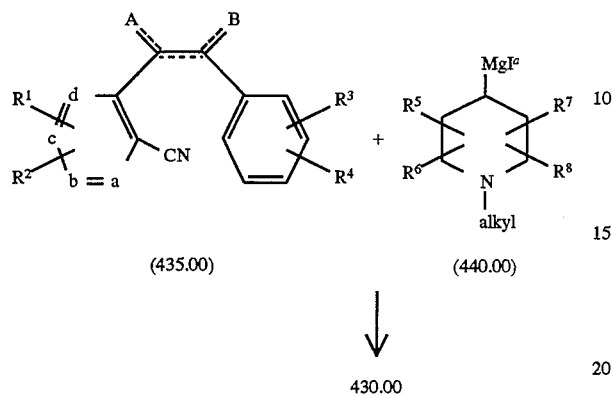

(435.00)   (440.00)

430.00

The cyano compound of Formula 435.00 is produced by converting the tertiary butyl amide of Formula 445.00 with a suitable dehydrating agent, such as POCl$_3$, SOCl$_2$, P$_2$O$_5$, toluene sulfonyl chloride in pyridine, oxalyl chloride in pyridine, etc. This reaction can be performed in the absence of or with a co-solvent, such as xylene.

The dehydrating agent such as POCl$_3$ is employed in equivalent amounts or greater and preferably in amounts of from about 2 to about 15 equivalents. Any suitable temperature and time can be employed for performing the reaction, but generally heat is added to accelerate the reaction. Preferably the reaction is performed at or near reflux.

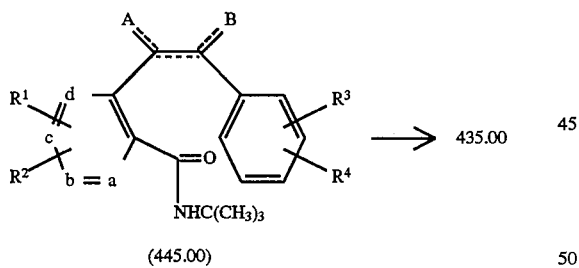

(445.00)

The tert-butylamide of Formula 445.00 may be produced by reaction of a compound of Formula 450.00a and 450.00b, in the presence of base, wherein G is chloro, bromo or iodo.

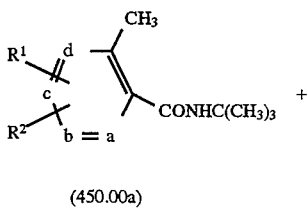

(450.00a)

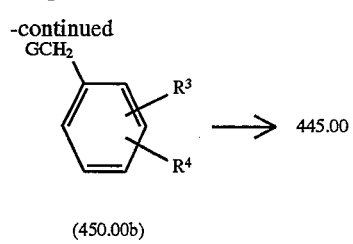

(450.00b)

The compound of Formula 450.00a may be formed by hydrolysis of the corresponding nitrile wherein the appropriate cyanomethyl pyridine, such as 2-cyano-3-pyridine, is reacted with a tertiary butyl compound in acid, such as concentrated sulfuric acid or concentrated sulfuric acid in glacial acetic acid. Suitable tertiary butyl compounds include, but are not limited to, t-butyl alcohol, t-butyl chloride, t-butyl bromide, t-butyl iodide, isobutylene or any other compound which under hydrolytic conditions forms t-butyl carboxamides with cyano compounds. The temperature of the reaction will vary depending upon the reactants, but generally the reaction is conducted in the range of from about 50° C. to about 100° C. with t-butyl alcohol. The reaction may be performed with inert solvents, but is usually run neat.

An alternative process for the formation of compounds of Formula 400.00a may involve direct cyclization of Compound 455.00 as shown below. Intermediates 400.00a and 455.00 can be converted to 405.00 similar to the conversion of intermediate 415.00 to 405.00.

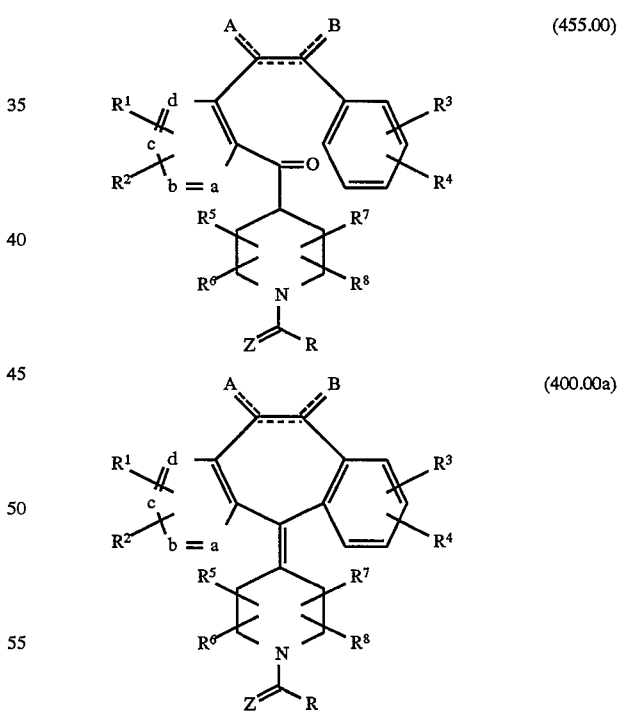

Cyclization to form the cycloheptene ring may be accomplished with a strong acid (e.g., triflic, polyphosphoric, HF/BF$_3$), and may be performed in an inert solvent, such as ether, toluene or THF. The temperature and time may vary with the acid employed, as described in process A above.

Compounds of Formula 455.00 may be prepared by treating a compound of Formula 425.00 with an appropriate chloroformate (such as ethyl chloroformate). Most preferably this reaction is run in the presence of a base (such as pyridine or triethylamine) in the appropriate solvent, such as toluene, dioxane or xylene, and at a temperature ranging from 50°–150° C., preferably 100°–120° C.

A second method of preparing compounds of Formula 455.00 involves reacting an unsubstituted piperidylidene compound of Formula 460.00 with the appropriate chloroformate (such as ethyl chloroformate) in the presence of base, such as pyridine or triethylamine, and an appropriate solvent (such as dichloromethane).

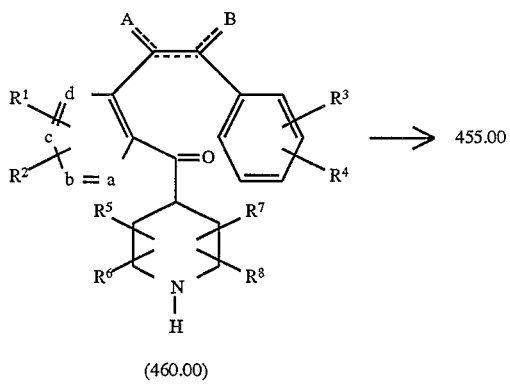

(460.00)

Compounds of Formula 460.00 may be produced from the corresponding carbamates of Formula 465.00, via acid hydrolysis, using for example, aqueous hydrochloric acid, or base hydrolysis using for example, potassium hydroxide. Alternatively, some compounds can be prepared by treating the carbamate, Formula 465.00, with an organometallic reagent, such as methyl lithium or a reductive reagent, such as zinc in acid, etc., depending upon the nature of the $R^a$ group. For example, if $R^a$ is a simple alkyl group, $CO_2R^a$ may be cleaved by alkaline hydrolysis at 100° C.

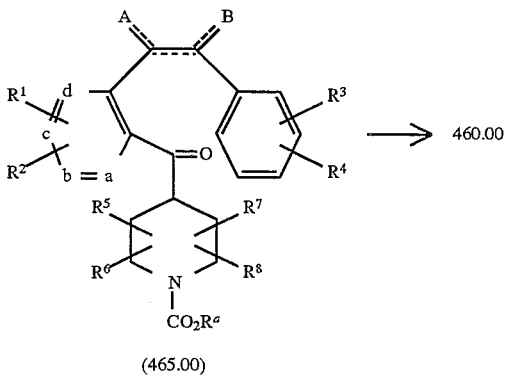

(465.00)

The carbamate compounds of Formula 465.00 may be prepared from the appropriate alkyl compound of Formula 425.00 by treatment with a chloroformate, preferably in an inert solvent, such as toluene, with warming to approximately 80° C. Other alternative methods are available for the conversion of 425.00 to 455.00 as previously described (e.g. Von Braun reaction conditions). Compounds of Formula 425.00 may be prepared as described above.

SUBSTITUTION ON THE PYRIDINE RING

Various methods can be used as described in WO 88/03138 to provide compounds which are substituted on the pyridine ring, i.e., in positions 2-, 3- and or 4- positions of the tricyclic ring system. For example, the cyclization methods described on pages 20–30 of WO 88/03138 can already have the appropriate substituents on the pyridine ring in place. A variety of substituted pyridines are known in the literature and can be employed in these syntheses. Alternatively, the azaketone of Formula XIX (from page 27 of WO 88/03138)

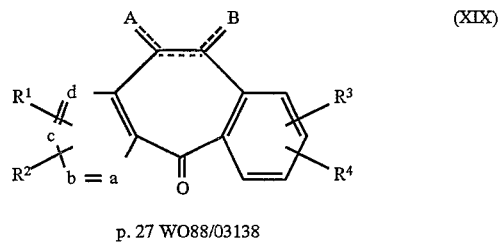

p. 27 WO88/03138 wherein $R^1$ and $R^2$ are both H can be converted to the appropriately substituted azaketone wherein $R^1$ and $R^2$ are non-H substitutents. If both $R^1$ and $R^2$ are desired to be non-H substitutents the procedure would be repeated.

The azaketone is thus reacted with an oxidizing agent such as meta-chloroperoxybenzoic acid (MCPBA) or hydrogen peroxide to produce the corresponding compound in which the nitrogen of the pyridine ring is an N-oxide;

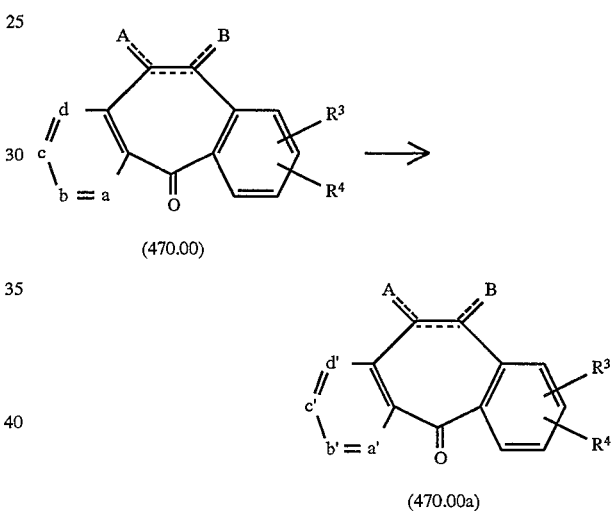

(470.00a)

wherein one of a', b', c' or d' is N→O and the others are CH or $CR^1$ or $CR^2$. This reaction is normally run at temperatures from −15° C. to reflux, more typically at about 0° C. The reaction is preferably conducted in an inert solvent such as methylene chloride for MCPBA or acetic acid for hydrogen peroxide.

The azaketone N-oxide of Formula 470.00a can then be reacted with a chlorinating agent such as $SO_2Cl_2$ or $SOCl_2$ to form a compound of Formula 470.00. Typically, this reaction results in monosubstitution of Cl in the ortho or para-position relative to the N atom of the ring.

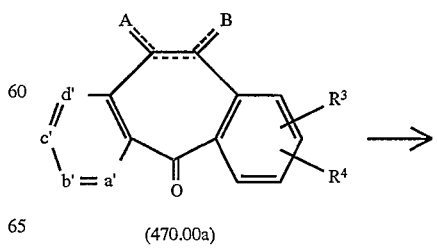

(470.00a)

-continued

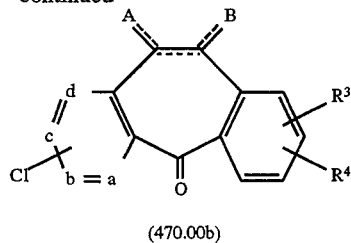
(470.00b)

To provide the disubstituted products, steps 1 and 2 above are repeated.

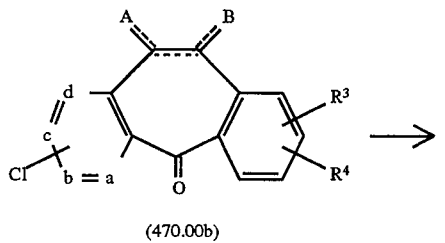
(470.00b)

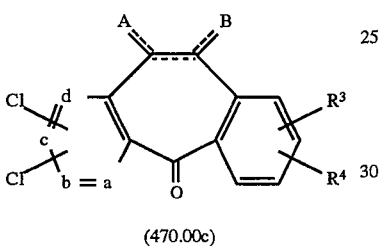
(470.00c)

Typically, the resulting disubstituted compounds have Cl ortho and para relative to the N atom of the pyridine ring.

The mono or disubstituted compounds of Formulas 470.00b and 470.00c above can be reacted with various nucleophiles such as alkoxides, amines, thiols, etc. This will result in compounds where one or both of the Cl substituents are replaced by the nucleophile to provide a compound of Formula 470.00d or a compound easily converted to Formula 470.00d.

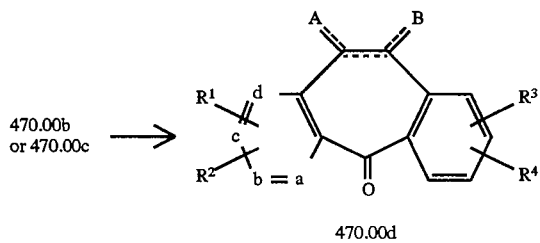
470.00d

The substituted ketone of Formula 470.00 can then be converted to the desired compound by the methods described above and in WO 88/03138 and in U.S. Pat. No. 3,326,924.

Alternatively, the Cl substituted azaketones of formula 470.00b or 470.00c above can be converted to the corresponding derivatives of Formula 405.00 above wherein $R^1$ and/or $R^2$ is Cl by methods analogous to those described above. At this point the Cl substituent(s) can be displaced by an appropriate nucleophile to provide the desired substituent. Suitable nucleophiles include alkoxide, amines, thiols, etc. This reaction usually requires higher temperatures (e.g., from about 100° to about 200° C.) than the displacement reaction to produce ketone 470.00d above. It is also usually conducted in a sealed vessel in an inert solvent. The compound of Formula 405.00 is then converted to a compound of Formula 400.00 as described above.

PREPARATION OF C5-C6-ENE DERIVATIVES

Compounds of formula 400.00 with a double bond between C-5 and C-6 can be prepared by heating a compound of Formula 470.00h in acetic acid with $SeO_2$ to produce a compound of Formula 470.00i. Compounds of Formula 470.00i can be converted to final products according to methods already described.

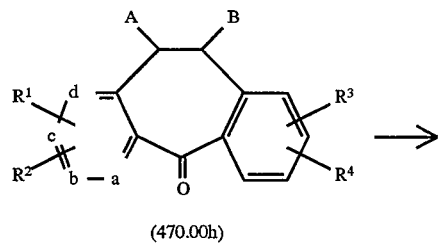
(470.00h)

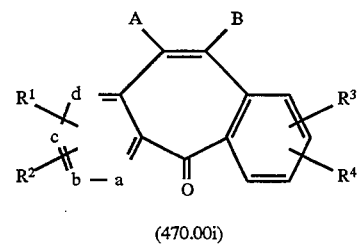
(470.00i)

PREPARATION OF PIPERAZINE ANALOGS

Compounds having a piperazine ring bound to the C-11 of the tricyclic nucleus, i.e., Formula 1.0 wherein X is N, are best prepared via alkylation of the appropriately substituted piperazine compound of Formula 700.00 with a compound of Formula 705.00. Compounds of Formula 705.00 contain the appropriately substituted halide (such as Cl, Br, or I) or other similar leaving group (e.g., tosyloxy or mesyloxy). The reaction is usually conducted in an inert solvent, such as THF or toluene, optionally with a base such as triethylamine or potassium carbonate, and typically at a temperature range of ambient to reflux to produce a compound of Formula 710.00.

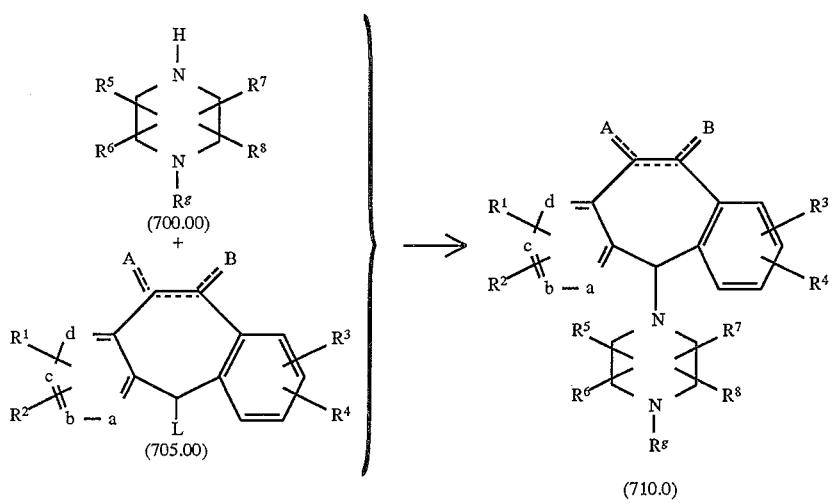

In this reaction $R^g$ is H or $CO_2R^a$ (wherein $R^a$ is a $C_1$ to $C_4$ alkyl group). The preparation of compound 705.00 wherein L is Cl is analogous to the procedure described in U.S. Pat. No. 3,409,621. By methods known in the art compounds of Formula 710.00, wherein $R^g$ is $CO_2R^a$, can be converted to Formula 710.00 wherein $R^g$ is H, by acid or base hydrolysis as described in U.S. Pat. No. 4,828,853. Compounds of formula 710.00, wherein $R^g$ is H, can be converted to compounds of Formula 400.00 by the process used to convert Formula 405.00 to Formula 400.00. Compounds of 410.00, wherein R is 3-pyridyloxy, can be prepared by reacting 3-hydroxypyridine with an excess of phosgene in toluene/dichloromethane at 0° C. in the presence of a base such as pyridine.

An alternate route for generating the compound of Formula 710.00 is by reductive amination of the aza ketone 715.00 with the piperazine 700.00

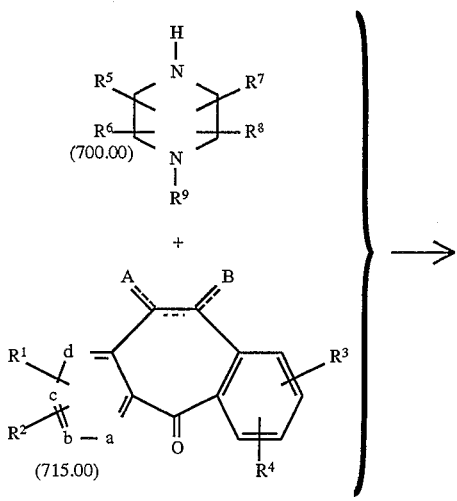

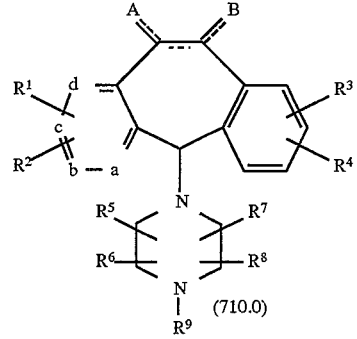

The reaction is typically carried out in a polar solvent, such as methanol or ethanol, optionally in the presence of a dehydrating agent, such as 3A molecular sieves. The intermediate Schiff base can be reduced to the compound of Formula 710.00 by employing a variety of reducing agents, such as $NaCNBH_3$, or catalytic hydrogenation, for example, hydrogen over Pd/C.

When $R^g$ is C(Z)R, these are the compounds of the invention.

An alternative process for introducing substituents at the C-3 position of pyridine Ring I of Formula 1.0, involves nitrating a compound of Formula 415.00 (except wherein X is nitrogen) or a compound of Formula 470.00d with tetrbutylammonium nitrate—trifluoroacetic anhydride in methylene chloride at a temperature of 0° C. to room temperature (about 25° C.). The nitro group may then be reduced to the corresponding amine using iron filings in ethanol, or powdered zinc—acetic acid in aqueous THF. By methods know to those skilled in the art, the amine group can be converted to a variety of substituents, such as, halo, cyano, thio, hydroxyl, alkyl, alkenyl, alkynyl and haloalkyl.

Compounds of formula 4.0 wherein $R^{30}$ represents a pyridyl N-oxide, can be produced by reacting compounds of formula 4.0, wherein $R^{30}$ is pyridyl, with a one molar equivalent of an oxidizing agent (such as oxone).

Various electrophilic species can also be added to the pyridine ring from the corresponding halo-substituted pyridine (Formula 405.00 wherein $R^1$ is halo, preferably bromo or iodo). Transmetallation of the halo derivative using an alkyl lithium (e.g. n-BuLi) provides the lithio derivative, which can then be quenched with the appropriate electrophile (e.g. $R^1L$, etc.).

In the above processes, it is sometimes desirable and/or necessary to protect certain $R^1$, $R^2$, $R^3$ and $R^4$ etc., groups during the reactions. Conventional protecting groups are operable as described in Greene, T. W., "Protective Groups In Organic Synthesis," John Wiley & Sons, New York, 1981. For example, the groups listed in column 1 of Table 1 may be protected as indicated in column 2 of the table:

TABLE 1

PROTECTED GROUPS

| 1. GROUP TO BE PROTECTED | 2. PROTECTED GROUP |
|---|---|
| —COOH | —COOalkyl, —COObenzyl, —COOphenyl, 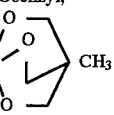 |
| \NH/ | \NCOalkyl/, \NCObenzyl/, \NCOphenyl/ |
| \CO/ |  |
| —OH | —O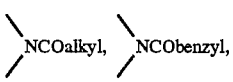, —OCH₂phenyl, —OCH₃, OSi(CH₃)₂(t-Bu), |
| —NHR, wherein R is any substituent on an amino group within the scope of the claims | 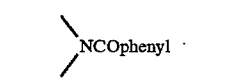, —NR—CO—CF₃, —NRCOCH₃, —NRCH₂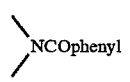 |
| —NH₂ | , —NH—C(O)—O(t-Bu) |

Other protecting groups well known in the art also may be used. After the reaction or reactions, the protecting groups may be removed by standard procedures.

Compounds useful in this invention are exemplified by the following preparative examples, which should not be construed to limit the scope of the disclosure. Alternative mechanistic pathways and analogous structures within the scope of the invention may be apparent to those skilled in the art.

PREPARATIVE EXAMPLE 1

A. N-(1,1-Dimethylethyl)-3-Methyl-2-Pyridine Carboxamide

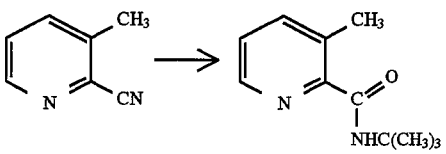

Suspend 2-cyano-3-methyl pyridine (400 g) in t-butanol (800 mL) and heat to 70° C. Add concentrated sulphuric acid (400 mL) dropwise over 45 minutes. Maintain the temperature at 75° C., until the reaction is complete, and for an additional 30 minutes. Dilute the mixture with water (400 mL), charge with toluene (600 mL) and bring to pH 10 with concentrated aqueous ammonia. Maintain the temperature at 50°–55° C. during the work up. Separate the toluene phase, and reextract the aqueous layer. Combine toluene phases and wash with water. Remove the toluene to yield the title compound N-(1,1-dimethylethyl)-3-methyl-2-pyridine carboxamide, as an oil, from which solid product is crystallized. (Yield 97%, as determined by an internal standard assay with gas chromatography).

B. 3-[2-(3-Chlorophenyl)Ethyl]-N-(1,1-Dimethylethyl)-2-Pyridine Carboxamide

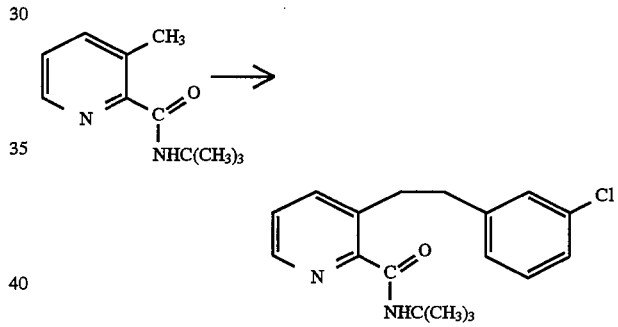

Dissolve the title compound of Preparative Example 1A, N-(1,1-dimethylethyl)-3-methyl-2-pyridine carboxamide (31.5 g.) in tetrahydrofuran (600 mL) and cool the resulting solution to –40° C. Add n-butyllithium (2 eq.) in hexane while maintaining the temperature at –40° C. The solution turns deep purple-red. Add sodium bromide (1.6 g) and stir the mixture. Add solution of m-chlorobenzylchloride (26.5 g., 0.174 mole) in tetrahydrofuran (125 mL) while maintaining the temperature at –40° C. Stir the reaction mixture until the reaction is complete as determined by thin layer chromatography. Add water to the reaction until the color is dissipated. Extract the reaction mixture with ethyl acetate, wash with water, and concentrate to a residue which is the title compound. (Yield 92% as shown by chromatography).

C. 3-[2-(3-Chlorophenyl)Ethyl]-2-Pyridine-Carbonitrile

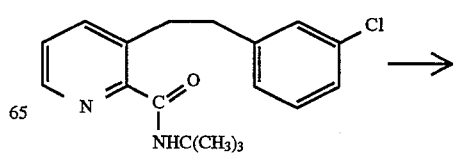

E. 8-Chloro-11-(1-Methyl-4-Piperidylidene)-6,11-Dihydro-5H-Benzo[5,6]Cyclohepta[1,2-b]Pyridine

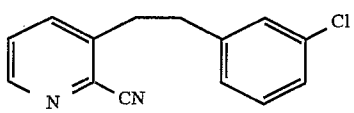

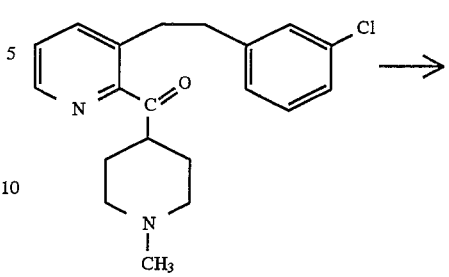

Heat a solution of the title compound of Preparative Example 1B, 3-[2-(3-chlorophenyl)ethyl]-N-(1,1-dimethylethyl)-2-pyridine carboxamide (175 g, 0.554 mole) in phosphorous oxychloride (525 mL, 863 g, 5.63 mole) and reflux for 3 hours. Determine completion of the reaction by thin layer chromatography. Remove any excess phosphorous oxychloride by distillation at reduced pressure and quench the reaction in a mixture of water and isopropanol. Bring to pH 5–7 by adding 50% aqueous sodium hydroxide solution while maintaining the temperature below 30° C. Filter the crystalline slurry of crude product and wash with water. Purify the crude product by slurrying the wet cake in hot isopropanol, and cool to 0°–5° C. Filter the product, wash with hexane and dry at a temperature below 50° C. to yield the title compound. (Yield: 118 g (HPLC purity 95.7%), m.p. 72° C.–73° C., 89.4% of theory).

D. 1-(Methyl-4-Piperidinyl)[3-(2-(3-Chlorophenyl)ethyl)-2-Pyridinyl]Methanone Hydrochloride

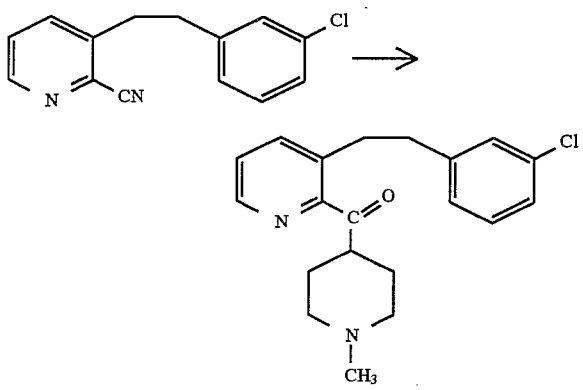

Dissolve the title compound of Preparative Example 1C, (118 g, 0.487 mole) in dry tetrahydrofuran (1.2 L) and add N-methyl-piperidyl magnesium chloride (395 mL, 2.48 mole/liter, 0.585 mole, 1.2 eq.) over 15 minutes. Maintain the temperature at 40° C.–50° C. by cooling with water as necessary, for 30 minutes. Determine completion of the reaction by thin layer chromatography. Quench the reaction by reducing the pH to below 2 with 2N HCl and stir the resulting solution at 25° C. for 1 hour. Remove the bulk of the tetrahydrofuran by distillation and adjust the resulting solution to pH 3.5 by addition of aqueous sodium hydroxide. Cool to 0° to 5° C. and filter off the crystalline hydrochloride salt product. Wash with ice cold water and dry to constant weight at 60° C. to yield the title compound. (Yield: 168.2 g (HPLC purity 94%), m.p. 183°–185° C., 89% of theory).

Dissolve the title compound of Preparative Example 1D above (59 g, 0.15 mole) in hydrofluoric acid (120 mL, 120 g, 6.0 mole) at −35° C. and add boron trifluoride (44.3 g, 0.66 mole) over 1 hour. Determine completeness of the reaction by thin layer chromatography. Quench the reaction using ice, water and potassium hydroxide bringing the solution to a final pH of 10. Extract the product with toluene and wash with water and brine. Concentrate the toluene solution to a residue, and dissolve in hot hexane. Remove the insolubles by filtration and concentrate the filtrate to yield the title compound as an off-white powder. (Yield: 45.7 g (HPLC purity: 95%), 92% of theory).

Alternative Step E: 8-Chloro-11-(1-Methyl-4-Piperidylidene)-6,11-Dihydro-5H-Benzo[5,6]Cyclohepta[1,2-b]Pyridine React the title compound of Preparative Example 1D above (177 g, 0.49 mole) in trifluoromethanesulfonic acid (480 ml, 814.1 g, 5.31 mole) at 90°–95° C. for 18 hours under nitrogen. Determine the completeness of the reaction by thin layer chromatography. Cool the reaction and quench the reaction with ice-water and adjust the pH to 6 with barium carbonate. Extract the product with methylene chloride, and concentrate under reduced pressure to about 1. liter. Wash with water, and extract the product into 1N HCl which is treated with 30 g of activated charcoal, and filter through celite. Adjust the pH of the filtrate to 10 with aqueous sodium hydroxide (50%), extract the product into methylene chloride, and remove under reduced pressure to form a residue. Dissolve the residue in hot hexane, and filter to remove insolubles. Concentrate the filtrate to yield the title compound as a beige powder. (Yield: 126 g (HPLC purity 80%), 65% of theory).

F. 8-Chloro-11-(1-Ethoxycarbonyl-4-Piperidylidene) 6,11-Dihydro-5H-Benzo[5,6]Cyclohepta[1,2-b] Pyridine

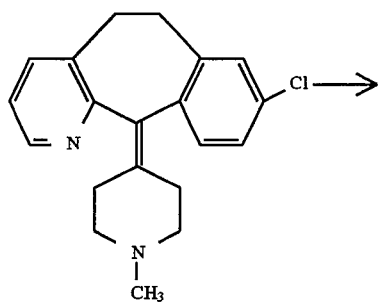

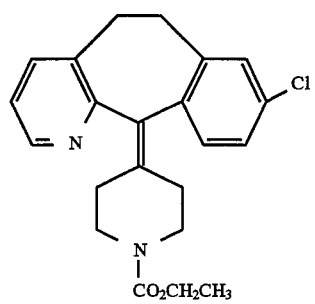

Dissolve the title compound of Preparative Example 1E above (45.6 g, 0.141 mole) in toluene (320 mL) at 80° C. and to it gradually add ethyl chloroformate (40.4 mL, 45.9 g, 0.423 mole). Following complete addition, maintain the temperature at 80° C. for 1 hour, then add diisopropylethylamine (2.7 mL, 2.00 g, 0.016 mole) and additional ethyl chloroformate (4.1 mL, 4.65 g, 0.0429 mole). Monitor completeness of the reaction by thin layer chromatography. Upon completion, cool the reaction mixture to ambient temperature, and wash the toluene solution with water. Concentrate the organic layer to a residue and dissolve in hot acetonitrile (320 mL). Decolorize the solution with 14 g of activated charcoal. Remove the activated charcoal by filtration and concentrate the filtrate to a crystalline slurry. Cool the mixture to 0°–5° C., and isolate the product by filtration. Wash with cold acetonitrile and dry the product at below 70° C. to yield the title compound, (Yield: 42.4 g (HPLC purity 97.4%), 80% of theory).

G. 8-Chloro-11-(4-Piperidylidene)-6,11-Dihydro-5H-Benzo[5,6]Cyclohepta[1,2-b]Pyridine

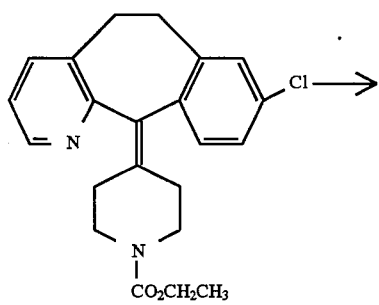

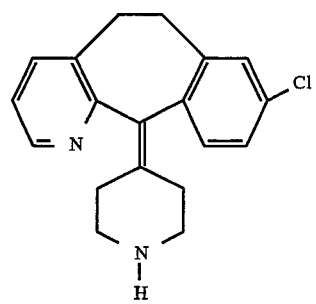

Hydrolize the title compound of Preparative Example 1F, 8-chloro-11-(1-ethoxycarbonyl-4-piperidylidene)-6,11-dihydro-5H-benzo[5,6]cyclohepta[1,2-b]pyridine (39 g, 0.101 mole) with KOH (50 g) in ethanol (305 mL) and water (270 mL) at reflux under an argon atmosphere for 64 hours. Partially distill off the ethanol and dilute the residue with brine, and extract with ethyl acetate (3x). Wash the combined organic phases with water and dry with $Na_2SO_4$. Remove the solvent to give a solid which can be recrystallized from toluene to give the title compound as a white solid. (Yield: 24.5 g, 77%, melting point 154°–155° C.).

PREPARATIVE EXAMPLE 2

8-Chloro-6,11-Dihydro-11-(4-Piperidinyl)-5H-Benzo[5,6]Cyclohepta[1,2-b]Pyridine (Product A) and 6,11-Dihydro-11-(4-Piperidinyl)-5H-Benzo[5,6]-Cyclohepta[1,2-b]Pyridine (Product B)

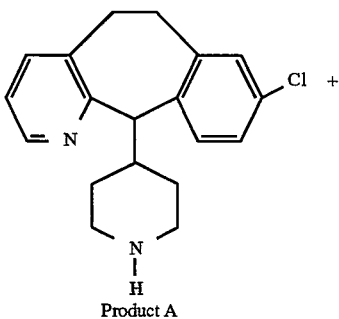

Product A

47

-continued

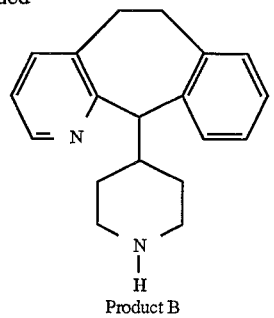
Product B

To a solution 66.27 g (0.21 mole) of 4-(8-chloro-5,6-dihydro-11H-benzo[5,6]cyclohepta(1,2-b]pyridin-11-ylidene)-piperidine (product from Preparative Example 1 Example, step G), in THF (1 L) was added lithium aluminum hydride (24.32 g, 0.64 mole) and the reaction mixture was heated to reflux overnight. The reaction mixture was then cooled to room temperature and ~3 L of diethyl ether is added followed by dropwise addition of saturated sodium sulfate until a white gray precipitate forms. Magnesium sulfate was then added to the separated organic layer and stirred for 30 minutes. All the volatiles were then removed and the resulting crude mixture was chromatographed on a silica gel column eluting with 10% methanol saturated with ammonia in methylene chloride. The material obtained contained both the desired compound and the des-chloro compound. Separation on HPLC using reverse phase column and eluting with 40% methanol-water afforded the desired compounds as white solids (Product A's mp=95.2°–96.1° C., Product B's mp=145.1°–145.7° C.).

PREPARATIVE EXAMPLE 3

Ethyl 4-(8-Chloro-6,11-Dihydro-5H-Benzo[5,6]
Cyclohepta(1,2-b]Pyridin-11-Yl)-1-Piperidine-
Carboxylate

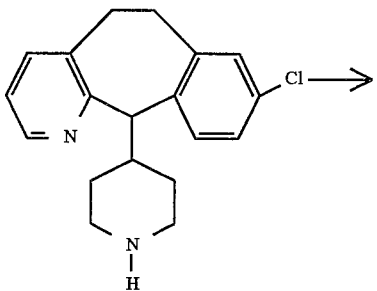

8-Chloro-6,11-dihydro-11-(4-piperidinyl)-5H-benzo[5,6] cyclohepta-[1,2-b]pyridine (product from Preparative Example 2) (4.18 g, 13 mmol) was dissolved in toluene (175 mL). Ethyl chloroformate(11.6 g, 110 mmol, 10.2 mL) was then added and the reaction mixture was heated to ~120° C. overnight. All volatiles were stripped off and the crude product was purified on silica gel column eluting with 50% ethyl acetate-hexanes to give the title compound as a white solid(MH⁺385).

PREPARATIVE EXAMPLE 4

A. 4-(8-Chloro-3-Nitro-5,6-Dihydro-11H-Benzo[5,6]-Cyclohepta[1,2-b]Pyridin-11-Ylidene)-1-Piperidine-1-Carboxylic Acid Ethyl Ester

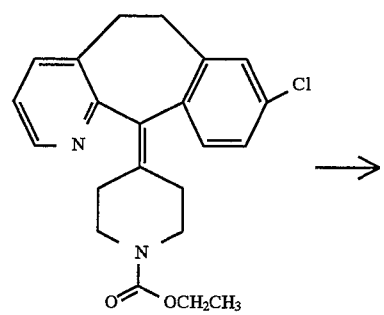

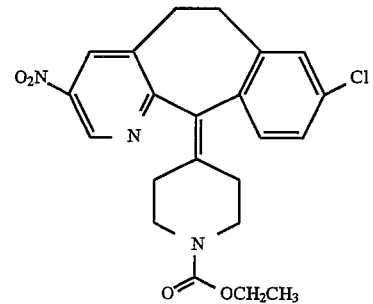

Tetrabutyl ammonium nitrate(4.98 g, 16.3 mmol) was dissolved in dichloromethane(20 mL) and trifluoroacetic anhydride(3.12 g, 14.9 mmol, 2.1 mL) was then added. The solution was cooled to 0° C. and then added (by cannulation) to a solution of 4-(8-chloro-5,6-dihydro-11H-benzo[5,6]-cyclohepta[1,2-b]pyridin-11-ylidene)-1-piperidine-1-carboxylic aid ethyl ester (5.69 g, 14.9 mmol) in methylene chloride (35 mL) also cooled to 0° C. The reaction mixture was stirred at 0° C. for 3 h and then allowed to go to room temperature (25° C.) overnight. The reaction mixture was then extracted with saturated sodium bicarbonate (60 mL) dried over magnesium sulfate and concentrated to give a semi-solid material that was chromatographed on silica gel eluting first with 10% and then 20% ethyl acetate-hexane. Removal of the organic solvents gave the title compound in 44% yield as a light yellow solid. MP=90.4°–91.0° C., MH⁺428.

B. 4-(8-Chloro-3-Amino-5,6-Dihydro-11H-Benzo[5,6]-Cyclohepta[1,2-b]Pyridin-11-Ylidene)-1-Piperidine-1-Carboxylic Acid Ethyl Ester

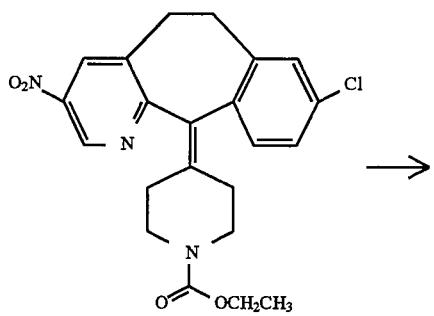

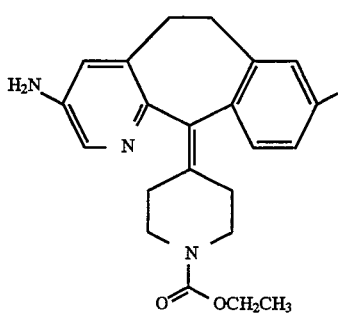

The title compound from Preparative Example 4A (5.99 g, 14 mmol) was dissolved in 85% aqueous ethanol. To this solution was added iron filings (7.01 g, 125.57 mmol) and calcium chloride (0.69 g, 6.29 mmol) and the reaction mixture was refluxed for 16 h. The reaction mixture was filtered through a bed of celite while hot and the celite was washed with hot ethanol (700 mL). The ethanol solution was then decolorized with activated charcoal (2.4 g) and then filtered through celite. Ethanol was then rotary eavaporated to give the title compound in 100% yield as an off-white solid. MP=102.4°–103.1° C., MH $^+$398.

C. 4-(8-Chloro-3-Bromo-5,6-Dihydro-11H-Benzo[5,6]-Cyclohepta[1,2-b]Pyridin-11-Ylidene)-1-Piperidine-1-Carboxylic Acid Ethyl Ester

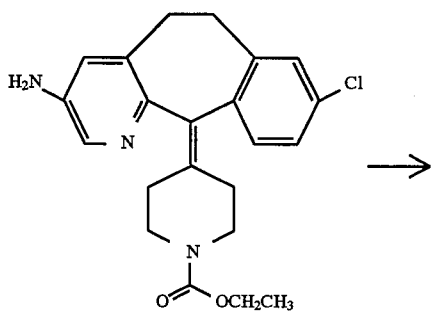

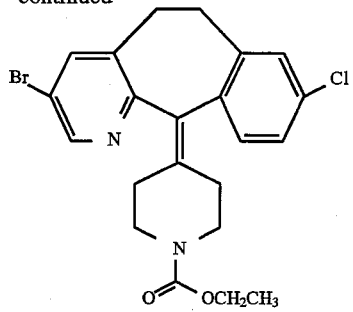

The title compound from Preparative Example 4B (3.00 g, 7.60 mmol) was dissolved in hydrobromic acid (48%, 30 mL). The reaction mixture was cooled to −5° C. (ice-ethylene glycol bath) and bromine(2 mL) was added dropwise. The reaction mixture was stirred at −5° C. for 15 minutes. Sodium nitrite (1.57 g, 22.8 mmol) dissolved in water (15 mL) was slowly added to the reaction mixture. The reaction mixture was then stirred for 45 minutes and then quenched with 40% NaOH to pH ~10. The aqueous phase was then extracted with ethyl acetate(3×100 mL). Combined ethyl acetate fractions were .dried over sodium sulfate and then concentrated to give the title compound in 83% yield as a light brown solid. Mp=146°–148° C., MH+463.

PREPARATIVE EXAMPLE 5

4-(8-Chloro-3-Nitro-5,6-Dihydro-11-(4-Piperidylidene)-11H-Benzo[5,6]Cyclohepta[1,2-b] Pyridine

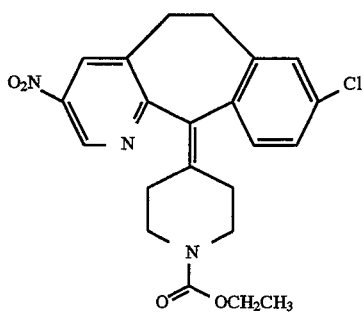

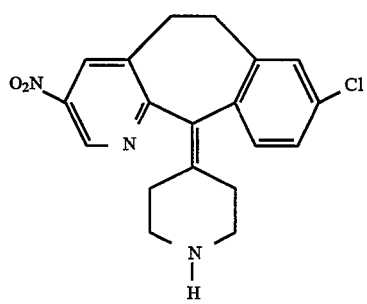

Hydrolyze the title compound of Preparative Example 4A (10.0 g, mmol) by dissolving in conc. HCl (250 mL) and heating to 100° C. for 16 h. The cooled acidic mixture was neutralized with 1M NaOH (950 mL). The mixture was extracted with methylene chloride. The latter was dried over magnesium sulfate. Filtration and concentration afforded the title compound in 99% yield as a solid. MH+358.

EXAMPLE 1

4-[8-Chloro-5,6-Dihydro-11H-Benzo-5,6]-Cyclohepta-[1,2-b]-Pyridin-11-Ylidene]-1-[Phenylmethylsulfonyl]-Piperidine

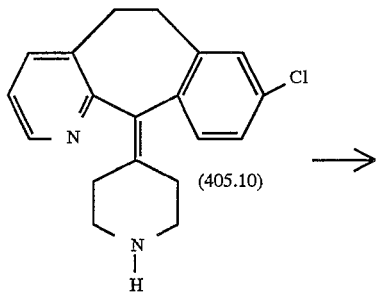

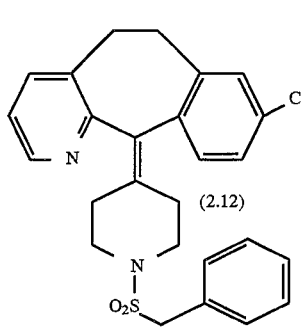

Suspend 0.8 g (5.79 mmole) of anhydrous potassium carbonate in 20 mL of toluene and add 0.5 g (1.61 Mmole) of 4-[8-chloro-5,6-dihydro-11H-benzo-[5,6]-cyclopenta-[1,2-b]-pyridin-11-ylidine]-piperidine (405.10) and 0.31 g (1.62 Mmole) of benzylsulfonyl chloride. Stir the mixture at 25° C. for two days and then filter the solid. Wash the filter cake with dichloromethane and then wash the filtrate with saturated sodium bicarbonate solution. Dry the organic layer over sodium sulfate, filter and concentrate the filtrate under vacuo. Chromatograph the resulting residue on silica gel using methanol and dichloromethane saturated with ammonia (8:92) to give the title compound as a white solid. Mass spec. $M^+=465$.

Compound 405.10 may be obtained in accordance with the procedures described above for compound 405.00.

In a manner similar to Example 1, the Compounds of Table 2 are prepared. The number in parenthesis in Column R of Table 2 refers to the compound of 2.0 produced for the particular R.

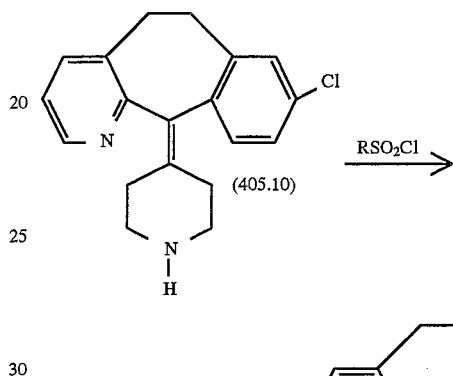

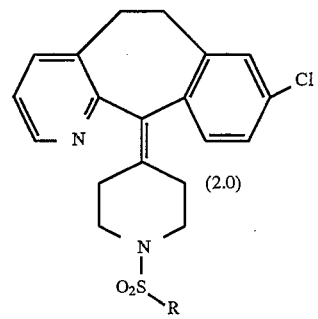

TABLE 2

| RSO₂Cl | R | Physical Date |
|---|---|---|
| C₄H₉SO₂Cl | —C₄H₉ (2.2) | Yellow solid mp = 180–182° C. Mass Spec M+ = 431 |
| C₂H₅SO₂Cl | —C₂H₅ (2.3) | Yellow solid mp = 180–182° C. Mass Spec M+ = 402 |
| 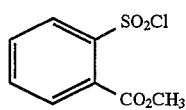 | 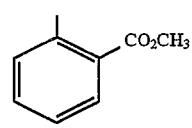 (2.4) | White solid mp = 110–111° C. Mass Spec M+ = 509 |
| 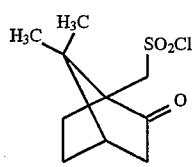 | 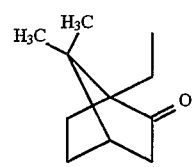 (2.5) | White solid mp = 225–227° C. Mass Spec M+ = 431 |

TABLE 2-continued

| RSO₂Cl | R | Physical Date |
|---|---|---|
| 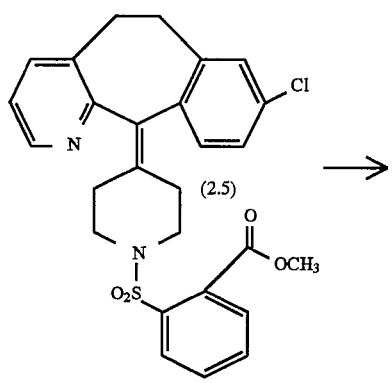 (structures shown) | (structures shown) | White solid mp = 200–202° C. Mass Spec M+ = 431 |
| | | White solid mp = 185–188° C. Mass Spec M+ = 529 (2.8) |
| | | White solid mp = 192–193° C. Mass Spec M+ = 400 (2.9) |

EXAMPLE 2

4-[8-Chloro-5,6-Dihydro-11H-Benzo-[5,6]-Cyclohepta-[1,2-b]-Pyridin-11-Ylidene]-1-[2-Carboxyphenylsulfonyl]-Piperidine

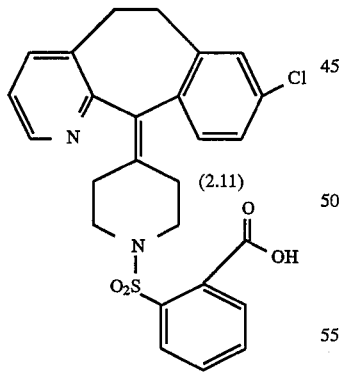

Dissolve 0.065 g (0.013 mmole) of Compound 2.5 (Table 2) in 5 mL of methanol and add 30 µL (2.5 equivalents) of 1N sodium hydroxide solution, and stir for four hours. Concentrate under vacuo and mix the residue with 5 mL of methanol and filter. Concentrate the filtrate under vacuo and mix the residue with 10 mL of ethyl acetate. Filter and concentrate the filtrate under vacuo to yield the sodium salt of the title compound as white solid, mp=100°–104° C. Mass Spec. M⁺=517.

EXAMPLE 3

(+)4-[8-Chloro-5,6-Dihydro-11H-Benzo-[5,6]-Cyclohepta-[1,2-b]-Pyridin-11-Ylidene]-1-[7,7-Dimethyl 5-Endo-Hydroxyl]Bicyclo[2.2.1]Hept-4-Methylsulfonyl]-Piperidine Dissolve 0.2 g (0.38 mmole) of Compound 2.6 from Table 2 in 5 mL of methanol and add 0.144 g (3.81 mmole) of sodium borohydride. Stir for six hours and concentrate under vacuo. Dissolve the residue in 50 mL of ethyl acetate and wash with 50 mL of water. Re-extract the water layer with two 50 mL portions of ethyl acetate. Combine the organic layers, wash with sodium bicarbonate solution, dry over sodium sulfate, and filter. Concentrate the filtrate under vacuo and chromatograph the residue on silica gel using 5% methanol, 95% dichloromethane saturated with ammonia, to give the title compound as a white solid, mp=136°–139° C., Mass Spec M$^+$=527.

EXAMPLE 4

Compounds of formulas 8.0–8.11, described above, wherein R$^{42}$ is e substituent selected from 8.12, 8.13, 8.14, 8.17, 8.18, 8.19, 8.22 or 8.23, could be prepared if one were to react a compound of formula 405.00, with substituents corresponding to the compounds of formulas 8.0–8.11, with R$^{42}$SO$_2$Cl by essentially the same procedure described in Example 1.

The compound R$^{42}$SO$_2$Cl, wherein R$^{42}$ represents 8.13, 8.14, 8.22, or 8.23, could be prepared by converting the alcohol, R$^{42}$OH, to the mesylate, R$^{42}$OSO$_2$CH$_3$, with one molar equivalent of methanesulfonyl chloride in the presence of a base (such as pyridine or triethylamine) in a solvent (such as methylene chloride or chloroform) at temperature of 0° to 25° C. The mesylate could be converted to the thiol, R$^{42}$SH, by reacting the mesylate with NaSH in a solvent (such as methanol or ethanol) at a temperature of 0° to 50° C. The thiol could be oxidized to the sulfonic acid, R$^{42}$SO$_3$H, by oxidizing agents (such as KMNO$_4$, or H$_2$O$_2$ in acetic acid). The sulfonic acid could be converted to the sulfonyl chloride, R$^{42}$SO$_2$Cl, by reacting the sulfonic acid with PCl$_5$.

The compound R$^{42}$SO$_2$Cl, wherein R$^{42}$ represents 8.18 or 8.19, could be prepared by reacting the amine, R$^{42}$NH$_2$, with SO$_2$Cl$_2$ in the presence of a base (such as pyridine or triethylamine) in a solvent (such as methylene chloride or chloroform) at temperature of 0° to 25° C.

EXAMPLE 5

Compounds of formulas 8.0–8.11, described above, wherein R$^{42}$ is a substituent selected from 8.15, 8.16, 8.20, or 8.21, could be prepared if one were to react a compound of formula 8.0–8.11, wherein R$^{42}$ is a substituent selected from 8.13, 8.14, 8.18 or 8.19, with a molar equivalent of oxone.

Those skilled in the art will appreciate that the starting reactant RSO$_2$Cl can be obtained by known methods. It will also be appreciated that other compounds useful in this invention can be produced in accordance with the procedures of Examples 1 to 5.

ASSAYS

1. In vitro enzyme assays: Inhibition of farnesyl protein transferase and geranylgeranyl protein transferase Both farnesyl protein transferase (FPT) and geranylgeranyl protein transferase (GGPT) I were partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyltransferase from bovine brain: Implications for protein prenylation specificity, Proc. Natl. Acad. Sci USA 88: 5302–5306, the disclosure of which is incorporated herein by reference thereto). Two forms of val$^{12}$-Ha-Ras protein were prepared as substrates for these enzymes, differing in their carboxy terminal sequence. One form terminated in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins were constructed so that the proteins contain an amino-terminal extension of 6 histidine residues. Both proteins were expressed in Escherichia coli and purified using metal chelate affinity chromatography. The radiolabelled isoprenyl pyrophosphate substrates, [$^3$H]farnesyl pyrophosphate and [$^3$H] geranylgeranyl pyrophosphate, were purchased from DuPont/New England Nuclear.

Several methods for measuring farnesyl protein transferase activity have been described (Reiss et al 1990, Cell 62: 81; Schaber et al 1990, J. Biol. Chem. 265: 14701; Manne et al 1990, PNAS 87: 7541; and Barbacid & Manne 1993, U.S. Pat. No. 5,185,248). The activity was assayed by measuring the transfer of [$^3$H]farnesyl from [$^3$H]farnesyl pyrophosphate to Ras-CVLS using conditions similar to those described by Reiss et al. 1990 (Cell 62: 81) The reaction mixture contained 40 mM Hepes, pH 7.5; 20 mM magnesium chloride; 5 mM dithiothreitol; 0.25 μM [$^3$H] farnesyl pyrophosphate; 10 μl Q-Sepharose-purified farnesyl protein transferase; the indicated concentration of tricyclic compound or dimethylsulfoxide (DMSO) vehicle control (5% DMSO final); and 5 μM Ras-CVLS in a total volume of 100 μl. The reaction was allowed to proceed for 30 minutes at room temperature and then stopped with 0.5 ml of 4% sodium dodecyl sulfate (SDS) followed by 0.5 ml of cold 30% trichloracetic acid (TCA). Samples were allowed to sit on ice for 45 minutes and precipitated Ras protein was then collected on GF/C filter paper mats using a Brandel cell harvester. Filter mats were washed once with 6% TCA, 2% SDS and radioactivity was measured in a Wallac 1204 Betaplate BS liquid scintillation counter. Percent inhibition was calculated relative to the DMSO vehicle control.

The geranylgeranyl protein transferase I assay was essentially identical to the farnesyl protein transferase assay described above, with two exceptions: [$^3$H] geranylgeranylpyrophosphate replaced farnesyl pyrophosphate as the isoprenoid donor and Ras-CVLL was the protein acceptor. This is similar to the assay reported by Casey et al (Casey, P. J., et al., (1991), Enzymatic modification of proteins with a geranylgeranyl isoprenoid, Proc. Natl. Acad. Sci, USA 88: 8631–8635, the disclosure of which is incorporated herein by reference thereto).

2. Cell-Based Assay: Transient expression of val$^{12}$-Ha-Ras-CVLS and va$^{12}$-Ha-Ras-CVLL in COS monkey kidney cells: Effect of farnesyl protein transferase inhibitors on Ras processing and on disordered cell growth induced by transforming Ras COS monkey kidney cells were transfected by electroporation with the plasmid pSV-SPORT (Gibco/BRL) containing a cDNA insert encoding either Ras-CVLS or Ras-CVLL, leading to transient overexpression of a Ras substrate for either farnesyl protein transferase or geranylgeranyl protein transferase I, respectively (see above).

Following electroporation, cells were plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media was removed and fresh media containing the appropriate drugs was re-added.

48 hours after electroporation cells were examined under the microscope to monitor disordered cell growth induced by transforming Ras. Cells expressing transforming Ras become more rounded and refractile and overgrow the monolayer, reminiscent of the transformed phenotype. Cells were then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 μM leupeptin; and 0.1 μM pepstatin. Cells were lysed by homogenization and cell debris was removed by centrifugation at 2000 × g for 10 min.

Cellular protein was precipitated by addition of ice-cold trichloroacetic acid and redissolved in 100 μl of SDS-electrophoresis sample buffer. Samples (5–10 μl) were loaded onto 14% polyacrylamide minigels (Novex, Inc.) and electrophoresed until the tracking dye neared the bottom of the gel. Proteins resolved on the gels were electroblotted onto nitrocellulose membranes for immunodetection.

Membranes were blocked by incubation overnight at 4° C. in PBS containing 2.5% dried milk and 0.5% Tween-20 and then incubated with a Ras-specific monoclonal antibody, Y13-259 (Furth, M. E., et al., (1982), Monoclonal antibodies to the p21 products of the transforming gene of Harvey murine sarcoma virus and of the cellular ras gene family, J. Virol. 43: 294–304), in PBS containing 1% fetal calf serum for one hour at room temperature. After washing, membranes were incubated for one hour at room temperature with a 1:5000 dilution of secondary antibody, rabbit anti-rat IgG conjugated to horseradish peroxidase, in PBS containing 1% fetal calf serum. The presence of processed and unprocessed Ras-CVLS or Ras-CVLL was detected using a colorimetric peroxidase reagent (4-chloro-1-naphthol) as described by the manufacturer (Bio-Rad). 3. Cell Mat Assay Normal human HEPM fibroblasts were planted in 3.5 cm dishes at a density of 5×10$^4$ cells/dish in 2 ml growth medium, and incubated for 3–5 d to achieve confluence. Medium was aspirated from each dish and the indicator tumor cells, T24-BAG4 human bladder carcinoma cells expressing an activated H-ras gene, were planted on top of the fibroblast monolayer at a density of 2×10$^3$ cells/dish in 2 ml growth medium, and allowed to attach overnight. Compound-induced colony inhibition was assayed by addition of serial dilutions of compound directly to the growth medium 24 h after tumor cell planting, and incubating cells for an additional 14 d to allow colony formation. Assays were terminated by rinsing monolayers twice with phosphate-buffered saline (PBS), fixing the monolayers with a 1% glutaraldehyde solution in PBS, then visualizing tumor cells by staining with X-Gal (Price, J., et al., Lineage analysis in the vertebrate nervous system by retrovirus-mediated gene transfer, Proc. Natl. Acad. Sci.84, 156–160 (1987)). In the colony inhibition assay, compounds were evaluated on the basis of two IC$_{50}$ values: the concentration of drug required to prevent the increase in tumor cell number by 50% (tIC$_{50}$) and the concentration of drug required to reduce the density of cells comprising the cell mat by 50% (mIC$_{50}$). Both IC$_{50}$ values were obtained by determining the density of tumor cells and mat cells by visual inspection and enumeration of cells per colony and the number of colonies under the microscope. The therapeutic index of the compound was quantitatively expressed as the ratio of mIC$_{50}$/tIC$_{50}$, with values greater than one indicative of tumor target specificity.

ASSAY DATA

The compounds listed in Table 3 refer to compounds of Formula 2.0:

TABLE 3

| COMPOUND | R | FPT IC$_{50}$ (μM) |
|---|---|---|
| 2.1 | —CH$_3$ | 1.9 |
| 2.2 | —C$_4$H$_9$ | 4.8 |
| 2.3 | —C$_2$H$_5$ | 5.2 |
| 2.4 | (o-methylbenzoyl-OCH$_3$ ester) | 10.6 |
| 2.5 | (dimethyl bicyclic ketone) | 11.4 |
| 2.6 | (2-thienyl methyl) | 13.0 |
| 2.8 | (thiazoline derivative) | 1% at 11.3 μM |
| 2.9 | (allyl) | 1.0 |
| 2.10 | (dimethyl bicyclic alcohol) | 8.2 |
| 2.11 | (o-methylbenzoic acid) | 20% at 10.8 μM |
| 2.12 | —CH$_2$—(phenyl) | 1.3 |
| 2.13 | —N(CH$_3$)$_2$ | 1.9 |

COMPOUND 3.4

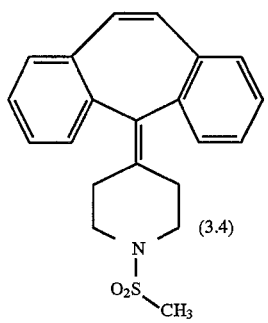

had a FPT IC$_{50}$ of 57 μM.

TABLE 4

COMPARISON OF FPT INHIBITION AND GGPT INHIBITION

| COMPOUND | ENZYME INHIBITION FPT IC$_{50}$ μM | ENZYME INHIBITION GGPT IC$_{50}$ μM |
|---|---|---|
| 2.1 | 1.9 | >51 (38%) |
| 2.12 | 1.3 | >42 (14%) |
| 2.13 | 1.9 | >48 (14%) |

TABLE 5

INHIBITION OF TUMOR CELL GROWTH - MAT ASSAY

| COMPOUND | INHIBITION OF TUMOR CELL GROWTH (IC$_{50}$ μM) | INHIBITION OF NORMAL CELL GROWTH (IC$_{50}$ μM) |
|---|---|---|
| 2.1 | 75.0 | >100.0 |
| 2.9 | 6.3 | 25.0 |
| 2.12 | >50.0 | >50.0 |
| 2.13 | 25.0 | 75.0 |

ACTIVITY IN COS CELLS

| COMPOUND | INHIBITION OF Ras PROCESSING IC$_{50}$ (μM) |
|---|---|
| 2.1 | >12.8 (0%) |
| 2.9 | <1.2 (57%) |
| 2.12 | >10.6 (30%) |
| 2.13 | >12.0 (0%) |

RESULTS

1. Enzymology

The data demonstrate that the compounds of the invention are inhibitors of Ras-CVLS farnesylation by partially purified rat brain farnesyl protein transferase (FPT). The data also show that there are compounds of the invention which can be considered as potent (IC$_{50}$<10 μM) inhibitors of Ras-CVLS farnesylation by partially purified rat brain farnesyl protein transferase (FPT)—see Table 3.

The data also demonstrate that compounds of the invention are poorer inhibitors of geranylgeranyl protein transferase (GGPT) assayed using Ras-CVLL as isoprenoid acceptor—see Table 4. Tested compounds weakly inhibited geranylgeranyl transferase at 20 μg/ml. Compound 2.1 inhibits GGPT 38% at 51 μM and is at least 27-fold selective for FPT inhibition. Compound 2.12 inhibits GGPT 14% at 42 μM and is at least 32-fold selective for FPT inhibition. Compound 2.13 inhibits GGPT 23% at 48 μM and is at least 25-fold selective for FPT inhibition. This selectivity is important for the therapeutic potential of the compounds used in the methods of this invention, and increases the potential that the compounds will have selective growth inhibitory properties against Ras-transformed cells. 2. Cell-Based: COS Cell and Cell Mat Assays Immunoblot analysis of the Ras protein expressed in Ras-transfected COS cells indicated that compound 2.9 inhibits Ras-CVLS processing, causing accumulation of unprocessed Ras-see Table 6. This compound inhibited processing 57% at 0.5 μg/ml, indicating an IC$_{50}$ value below 1.2 μM. Compounds 2.1 and 2.13 were inactive and compound 2.12 was weakly active when tested at 5 μg/ml—see Table 6. These results show that the compounds can inhibit farnesyl protein transferase in intact cells and indicate their potential to block cellular transformation by activated Ras oncogenes.

Compound 2.9 also inhibited the growth of Ras-transformed tumor cells in the Mat assay with an IC$_{50}$ value of 6.3 μM. This compound only displayed cytotoxic activity against the normal cell monolayer at higher concentrations (IC$_{50}$ of 25 μM). Compounds 2.1 and 2.12 tested in this assay had only weak antiproliferative activity against Ras-transformed cells—see Table 5.

IN VIVO ANTI-TUMOR STUDIES

Tumor cells (5×10$^5$ to 8×10$^6$ of A431[human epidermal carcinoma] or SW620 [human colon adenocarcinoma (lymph node metastasis)]) are innoculated subcutaneously into the flank of 5–6 week old athymic nu/nu female mice. For the C-f-1 [mouse fibroblast transformed with c-fos oncogene] tumor model, 2 mm$^3$ tumor fragments are transplanted subcutaneously into the flank of 5–6 week old athymic nu/nu female mice. Tumor bearing animals are selected and randomized when the tumors are established. Animals are treated with vehicle (beta cyclodextran for i.p. or corn oil for p.o.) only or compounds in vehicle twice a day (BID) for 5 (1–5) days per week for 2 (×2) or 4 (×4) weeks. The percent inhibition of tumor growth relative to vehicle controls are determined by tumor measurements. The results are reported in Table 7.

TABLE 7

IN-VIVO ANTI-TUMOR RESULTS

| s.c. TUMOR | ROUTE & SCHEDULE | COMPOUND 2.1 |
|---|---|---|
| A431 | ip, BID, 1–5, ×4 | 0 |
| C-f-1 | ip, BID, 1–5, ×2 | 0 |
| SW620 | ip, BID, 1–5, ×4 | 0 |
| SW620 | po, BID, 1–5, ×2 | 8 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as am conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

PHARMACEUTICAL DOSAGE FORM EXAMPLES

Example A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, | 30 | 40 |
|  | as a 10% paste in Purified Water |  |  |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for inhibiting farnesyl protein transferase in a patient in need of such treatment comprising administering an effective amount of a compound of Formula 1.0:

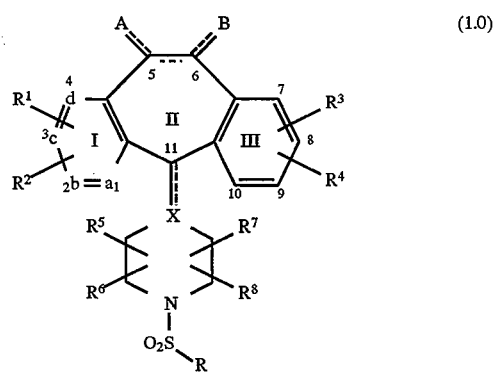

or a pharmaceutically acceptable salt or solvate thereof, wherein:

one of a, b, c and d represents N or NR$^9$ wherein R$^9$ is O$^-$, —CH$_3$ or —(CH$_2$)$_n$CO$_2$H wherein n is 1 to 3, and the remaining a, b, c and d groups represent CR$^1$ or CR$^2$;

R$^1$ and R$^2$ are the same or different and each independently represents H, benzotriazol-1yloxy, halo, —CF$_3$, —OR$^{10}$, —COR$^{10}$, —SR$^{10}$, —S(O)$_t$R$^{11}$ (wherein t is 0, 1 or 2), —N(R$^{10}$)$_2$, —NO$_2$, —OC(O)R$^{10}$, —CO$_2$R$^{10}$, —OCO$_2$R$^{11}$, —CN, —NR$^{10}$COOR$^{11}$, alkynyl, alkenyl or alkyl, which alkyl or alkenyl group may be substituted with halo, —OR$^{10}$ or —CO$_2$R$^{10}$;

R$^3$ and R$^4$ are the same or different and each independently represents any of the substituents of R$^1$ and R$^2$, or R$^3$ and R$^4$ together may represent a saturated or unsaturated C$_5$-C$_7$ ring fused to the benzene ring;

R$^5$, R$^6$, R$^7$ and R$^8$ each independently represent H, —CF$_3$, —COR$^{10}$, alkyl or C$_6$ to C$_{15}$ aryl, which alkyl or aryl may be substituted with —OR$^{10}$, —SR$^{10}$, S(O)$_t$R$^{11}$, —NR$^{10}$COOR$^{11}$, —N(R$^{10}$)$_2$, —NO$_2$, —COR$^{10}$, —OCOR$^{10}$, —OCO$_2$R$^{11}$, —CO$_2$R$^{10}$, OPO$_3$R$^{10}$ or one of R$^5$, R$^6$, R$^7$ and R$^8$ may be taken in combination with R as defined below to represent —(CH$_2$)$_r$— wherein r is 1 to 4 which may be substituted with lower alkyl, lower alkoxy, —CF$_3$ or C$_6$ to C$_{15}$ aryl;

R$^{10}$ represents H, alkyl or C$_6$ to C$_{15}$ aryl;

R$^{11}$ represents alkyl or C$_6$ to C$_{15}$ aryl;

X represents N or C, which C may contain an optional double bond to carbon atom 11;

the dotted lines represent optional double bonds;

the dotted line between carbon atoms 5 and 6 represents an optional double bond, such that when a double bond is present, A and B independently represent —R$^{10}$, —OR$^{11}$, —OC(O)R$^{11}$ or —OC(O)R$^{10}$, and when no double bond is present between carbon atoms 5 and 6, A and B each independently represent H$_2$, —(OR$^{11}$)$_2$, H and halo, dihalo, alkyl and H, (alkyl)$_2$, —H and —OC(O)R$^{10}$, H and —OR$^{10}$, =O, C$_6$ to C$_{15}$ aryl and H, =NOR$^{10}$ or —O—(CH$_2$)$_p$—O— wherein p is 2, 3 or 4;

R is selected from the group consisting of:
(1) C$_1$ to C$_4$ alkyl;
(2) phenyl substituted with 1 to 3 substituents selected from R$^1$, R$^2$ or C(O)OR$^{20}$, wherein R$^{20}$ is selected from the group consisting of: C$_1$ to C$_6$ alkyl and H;
(3) bridged polycyclic hydrocarbons selected from adamantyl, norbornyl or norcamphoryl;
(4) substituted bridged polycyclic hydrocarbons, wherein the bridged unsubstituted polycyclic hydrocarbon is selected from adamantyl, norbornyl or norcamphoryl, wherein the substituents are selected from the group consisting of C$_1$ to C$_6$ alkyl, said substituted bridged polycyclic hydrocarbon having from 1 to 8 substituents, and each substituent being the same or different;
(5) —(CH)$_2$R$^{21}$ wherein R$^{21}$ is C$_6$ to C$_{15}$ aryl, heteroaryl wherein said heteroaryl has at least one heteroatom selected from O, S, or N and has from 2 to 14 carbon atoms, 2-,3- or 4-piperidyl or N-substituted piperidyl, wherein the substituent on said N-substituted piperidyl is C$_1$ to C$_4$ alkyl, alkylcarbonyl or —C(O)NH(R$^{10}$) wherein R$^{10}$ is H or alkyl, a bridged polycyclic hydrocarbon selected from adamantyl, norbornyl or norcamphoryl, or a substituted bridged polycyclic hydrocarbon wherein the bridged unsubstituted polycyclic hydrocarbon is selected from adamantyl, norbornyl or norcamphoryl and wherein the substituents are selected from the group consisting of C$_1$ to C$_6$ alkyl and wherein said substituted bridged polycyclic hydrocarbon having from 1 to 8 substituents, and each substituent being the same or different;
(6) heteroaryl wherein said heteroaryl has at least one heteroatom selected from O, S, or N and has from 2 to 14 carbon atoms;
(7) substituted heteroaryl wherein said substituents are selected from the group consisting of: C$_1$ to C$_6$ alkyl and —NHC(O)R$^{22}$ wherein R$^{22}$ is a C$_1$ to C$_6$ alkyl and wherein said heteroaryl has at least one heteroatom selected from O, S, or N and has from 2 to 14 carbon atoms;
(8) C$_2$ to C$_6$ alkenyl; and
(9) —N(R$^{23}$)$_2$ wherein each R$^{23}$ is independently selected from the group consisting of: C$_1$ to C$_6$ alkyl, H, C$_6$ to C$_{15}$ aryl, 2-,3- or 4-piperidyl or N-substituted piperidyl, wherein the substituent on said N-substituted piperidyl is C$_1$ to C$_4$ alkyl, alkylcarbonyl or —C(O)NH(R$^{10}$) wherein R$^{10}$ is H or alkyl, heteroaryl wherein said heteroaryl has at least one heteroatom selected from O, S, or N and has from 2 to 14 carbon atoms, each R$^{23}$ is selected such that there is no more than one H bound to the nitrogen.

2. The method of claim 1 wherein a is N and b, c, and d are carbon; R$^1$ and R$^2$ are individually selected from H, —CF$_3$, C$_1$ to C$_4$ alkyl, benzotriazol-1yloxy or halo; R$^4$ is at the C-8 position and R$^3$ is at the C-9, and R$^3$ and R$^4$ are individually selected from H and halo; and R$^5$, R$^6$, R$^7$, and R$^8$ are H.

3. The method of claim 2 wherein R$^1$ and R$^2$ are independently selected from H, C$_1$ to C$_4$ alkyl, benzotriazol-1yloxy or halo; R$^4$ is Cl; R$^3$ is H; and R represents —N(R$^{23}$)$_2$, C$_1$–C$_4$ alkyl, C$_2$–C$_6$ alkenyl, —CH$_2$R$^{21}$ wherein R$^{21}$ is C$_6$ to C$_{15}$ aryl, heteroaryl wherein said heteroaryl has at least one heteroatom selected from O, S, or N and has from 2 to 14 carbon atoms, or 3- or 4-piperidyl or N-substituted piperidyl, wherein the substituent on said N-substituted piperidyl is C$_1$ to C$_4$ alkyl, alkylcarbonyl or —C(O)NH(R$^{10}$) wherein R$^{10}$ is H or alkyl.

4. The method of claim 3 wherein R represents —CH=CH$_2$, —CH$_2$C$_6$H$_5$, —CH$_2$R$^{21}$ wherein R$^{21}$ is 3-pyridyl, 4-pyridyl, 3-pyridyl N-oxide, 4-pyridyl N-oxide, 3-piperidyl, 3-N-substituted piperidyl, 4-piperidyl, or 4-N-substituted piperidyl, wherein the substituent on said N-substituted piperidyl is methyl.

5. The method of claim 4 wherein when there is a single bond between C-5 and C-6, A and B both represent H$_2$; and when there is a double bond between C-5 and C-6, A and B both represent H.

6. The method of claim 5 wherein the compound is selected from a compound of the structure:

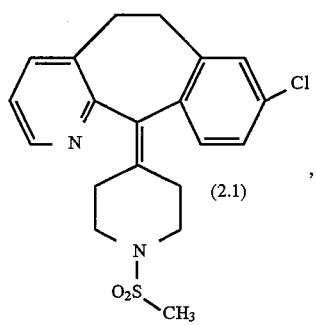

(2.1)

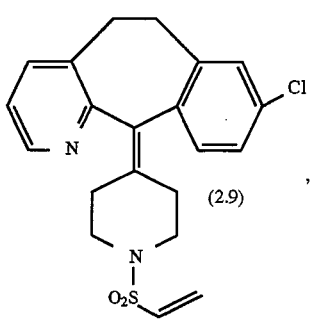
(2.9),
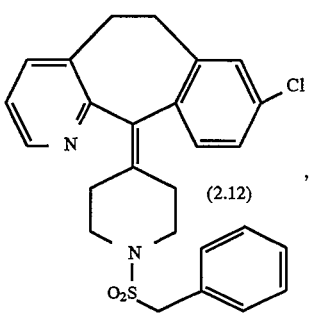
(2.12),
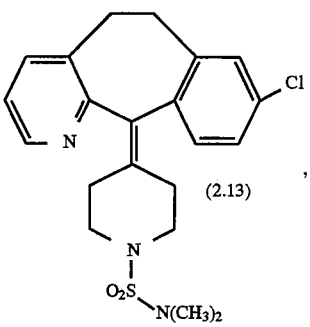
(2.13),
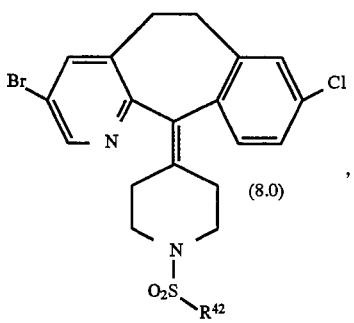
(8.0),
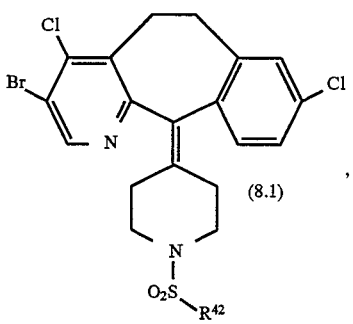
(8.1),
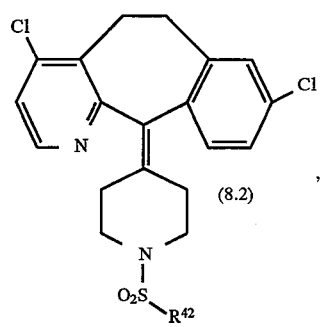
(8.2),
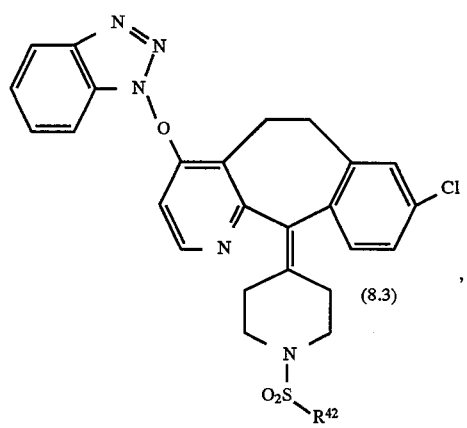
(8.3),
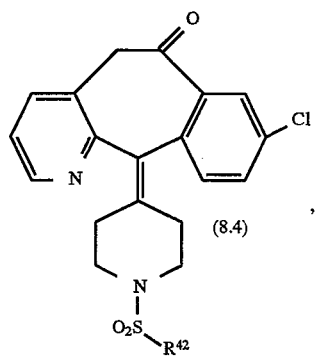
(8.4),
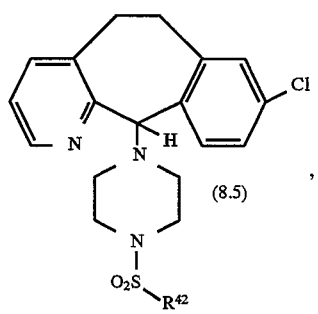
(8.5),

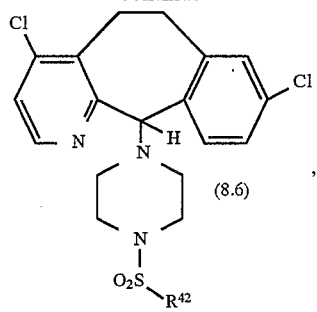
(8.6),
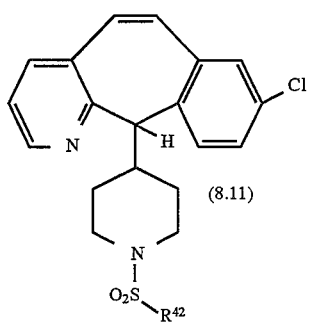
(8.11)
wherein R⁴² is selected from:
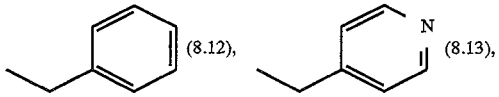
(8.12), (8.13),
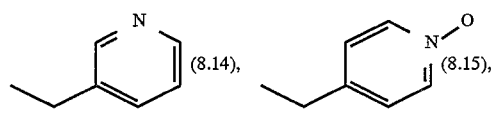
(8.14), (8.15),
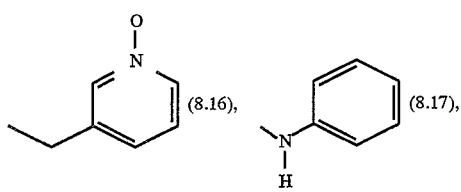
(8.16), (8.17),
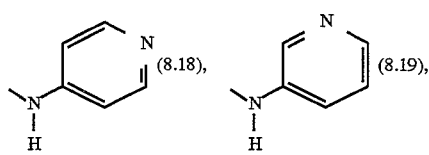
(8.18), (8.19),
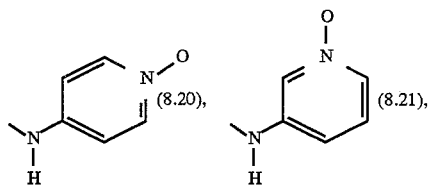
(8.20), (8.21),
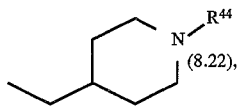
(8.22),
or
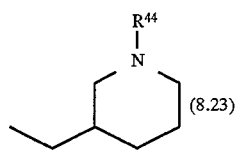
(8.23)
wherein $R^{44}$ is selected from H, alkyl, alkylcarbonyl, alkoxycarbonyl or —C(O)NHR¹⁰ wherein $R^{10}$ is H or alkyl.

7. A compound of formula 4.0:

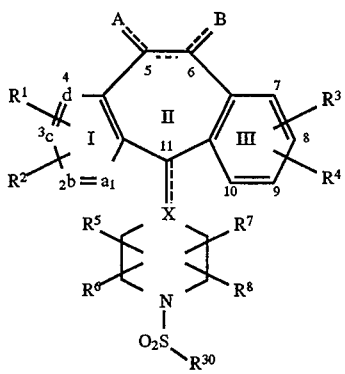

or a pharmaceutically acceptable salt or solvate thereof, wherein:

one of a, b, c and d represents N or NR$^9$ wherein R$^9$ is O$^-$, —CH$_3$ or —(CH$_2$)$_n$CO$_2$H wherein n is 1 to 3, and the remaining a, b, c and d groups represent CR$^1$ or CR$^2$;

R$^1$ and R$^2$ are the same or different and each independently represents H, benzotriazol-1yloxy, halo, —CF$_3$, —OR$^{10}$, —COR$^{10}$, —SR$^{10}$, —S(O)$_t$R$^{11}$ (wherein t is 0, 1 or 2), —N(R$^{10}$)$_2$, —NO$_2$, —OC(O)R$^{10}$, —CO$_2$R$^{10}$, —OCO$_2$R$^{11}$, —CN, —NR$^{10}$COOR$^{11}$, alkynyl, alkenyl or alkyl, which alkyl or alkenyl group may be substituted with halo, —OR$^{10}$ or —CO$_2$R$^{10}$;

R$^3$ and R$^4$ are the same or different and each independently represents any of the substituents or R$^1$ and R$^2$, or R$^3$ or R$^4$ together may represent a saturated or unsaturated C$_5$–C$_7$ ring fused to the benzene ring;

R$^5$, R$^6$, R$^7$ and R$^8$ each independently represent H, —CF$_3$, —COR$^{10}$, alkyl or C$_6$ to C$_{15}$ aryl, which alkyl or aryl may be substituted with —OR$^{10}$, —SR$^{10}$, S(O)$_t$R$^{11}$, —NR$^{10}$COOR$^{11}$, —N(R$^{10}$)$_2$, —NO$_2$, —COR$^{10}$, —OCOR$^{10}$, —OCO$_2$R$^{11}$, —CO$_2$R$^{10}$, OPO$_3$R$^{10}$ or one of R$^5$, R$^6$, R$^7$ and R$^8$ may be taken in combination with R as defined below to represent —(CH$_2$)$_r$— wherein r is 1 to 4 which may be substituted with lower alkyl, lower alkoxy, —CF$_3$ or aryl;

R$^{10}$ represents H, alkyl or C$_6$ or C$_{15}$ aryl;

R$^{11}$ represents alkyl or C$_6$ to C$_{15}$ aryl;

X represents N or C, which C may contain an optional double bond to carbon atom 11;

the dotted lines represent optional double bonds;

the dotted line between carbon atoms 5 and 6 represents an optional double bond, such that when a double bond is present, A and B independently represent —R$^{10}$, —OR$^{11}$, —OC(O)R$^{11}$ or —OC(O)R$^{10}$, and when no double bond is present between carbon atoms 5 and 6, A and B each independently represent H$_2$, —(OR$^{11}$)$_2$, H and halo, dihalo, alkyl and H, (alkyl)$_2$, —H and —OC(O)R$^{10}$, H and —OR$^{10}$, =O, C$_6$ to C$_{15}$ aryl and H, =NOR$^{10}$ or —O— (CH$_2$)$_p$—O— wherein p is 2, 3 or 4;

R$^{30}$ represents:

(1) bridged polycyclic hydrocarbons selected from adamantyl, norbornyl or norcamphoryl;

(2) substituted bridged polycyclic hydrocarbons, wherein the bridged unsubstituted polycyclic hydrocarbon is selected from adamantyl, norbornyl or norcamphoryl, wherein the substituents are selected from the group consisting of C$_1$ to C$_6$ alkyl, said substituted bridged polycyclic hydrocarbon having from 1 to 8 substituents with two being preferred, and each substituent being the same or different;

(3) —CH$_2$R$^{32}$ wherein R$^{32}$ is, heteroaryl wherein said heteroaryl has at least one heteroatom selected from O, S, or N and has from 2 to 14 carbon atoms, 2-,3- or 4-piperidyl or N-substituted piperidyl, wherein the substituent on said N-substituted piperidyl is C$_1$ to C$_4$ alkyl, alkylcarbonyl or —C(O)NH(R$^{10}$) wherein R$^{10}$ is H or alkyl, a bridged polycyclic hydrocarbon selected from adamantyl, norbornyl or norcamphoryl, or a substituted bridged polycyclic hydrocarbon as described above in paragraph (2);

(4) heteroaryl wherein said heteroaryl has at least one heteroatom selected from O, S, or N and has from 2 to 14 carbon atoms;

(5) substituted heteroaryl wherein said heteroaryl has at least one heteroatom selected from O, S, or N and has from 2 to 14 carbon atoms and wherein said substituents are selected from the group consisting of: C$_1$ to C$_6$ alkyl and —NHC(O)R$^{22}$ wherein R$^{22}$ is a C$_1$ to C$_6$ alkyl;

(6) C$_2$ to C$_6$ alkenyl; or (7) —N(R$^{40}$)$_2$ wherein each R$^{40}$ is independently selected from the group consisting of: H, C$_6$ to C$_{15}$ aryl, heteroaryl wherein said heteroaryl has at least one heteroatom selected from O, S, or N and has from 2 to 14 carbon atoms, and 2-,3- or 4-piperidyl or N-substituted piperidyl, wherein the substituent on said N-substituted piperidyl is C$_1$ to C$_4$ alkyl, alkylcarbonyl or —C(O)NH(R$^{10}$) wherein R$^{10}$ is H or alkyl.

8. The compound of claim 7 wherein a is N and b, c, and d are carbon; R$^1$ and R$^2$ are individually selected from H, —CF$_3$, C$_1$ to C$_4$ alkyl, benzotriazol-1yloxy or halo; R$^4$ is at the C-8 position and R$^3$ is at the C-9, and R$^3$ and R$^4$ are individually selected from H and halo; and R$^5$, R$^6$, R$^7$, and R$^8$ are H.

9. The compound of claim 8 wherein R$^1$ and R$^2$ are independently selected from H, C$_1$ to C$_4$ alkyl, benzotriazol-1yloxy or halo; R$^4$ is Cl; R$^3$ is H; and R$^{30}$ represents —N(R$^{40}$)$_2$, C$_2$–C$_6$ alkenyl, —CH$_2$R$^{32}$ wherein R$^{32}$ is heteroaryl, or 3- or 4-piperidyl or N-substituted piperidyl, wherein the substituent on said N-substituted piperidyl is C$_1$ to C$_4$ alkyl, alkylcarbonyl or —C(O)NH(R$^{10}$) wherein R$^{10}$ is H or alkyl.

10. The compound of claim 9 wherein R$^{30}$ represents —CH=CH$_2$, —CH$_2$R$^{21}$ wherein R$^{21}$ is 3-pyridyl, 4-pyridyl, 3-pyridyl N-oxide, 4-pyridyl N-oxide, 3-piperidyl, 3-N-substituted piperidyl, 4-piperidyl, or 4-N-substituted piperidyl, wherein the substituent on said N-substituted piperidyl is methyl.

11. The compound of claim 10 wherein when there is a single bond between C-5 and C-6, A and B both represent H$_2$; and when there is a double bond between C-5 and C-6, A and B both represent H.

12. The compound of claim 7 having the formula:

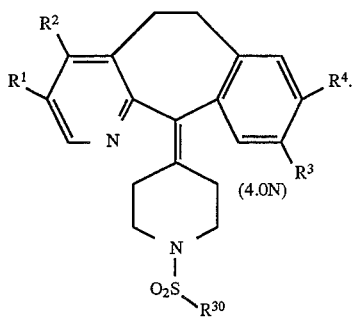

(4.0N)

wherein $R^1$ and $R^2$ independently represent H, halo, $C_1$ to $C_4$ alkyl or benzotriazol-lyloxy; $R^4$ is Cl; $R^3$ is H; and $R^{30}$ represents $C_2$-$C_6$ alkenyl, —$CH_2R^{32}$ wherein $R^{32}$ is heteroaryl, 3- or 4-piperidyl or N-substituted piperidyl, wherein the substituent on said N-substituted piperidyl is $C_1$ to $C_4$ alkyl, alkylcarbonyl or —C(O)NH($R^{10}$) wherein $R^{10}$ is H or alkyl, and —N($R^{40}$)$_2$.

13. The compound of claim 12 wherein $R^{30}$ represents —CH=$CH_2$, —$CH_2R^{32}$ wherein $R^{32}$ is 3-pyridyl, 4-pyridyl, 3-pyridyl N-oxide, 4-pyridyl N-oxide, 3-piperidyl, 3-N-substituted piperidyl, 4-piperidyl, 4-N-substituted piperidyl, wherein the substituent on said N-substituted piperidyl is methyl.

14. The compound of claim 7 wherein the compound is selected from a compound of the structure:

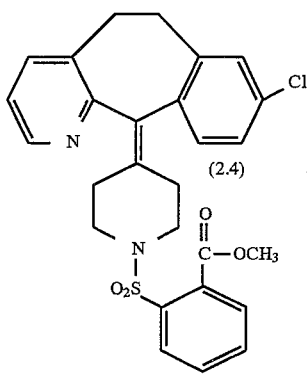

(2.4)

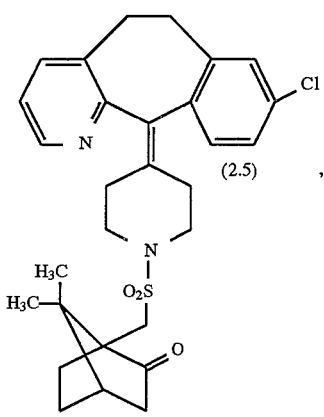

(2.5)

-continued

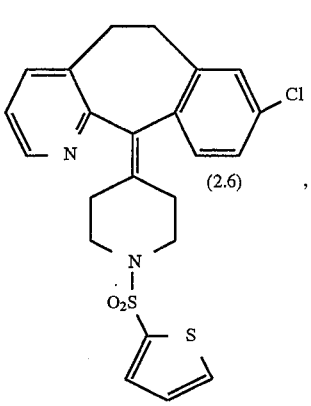

(2.6)

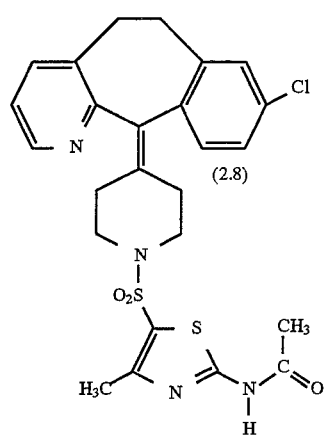

(2.8)

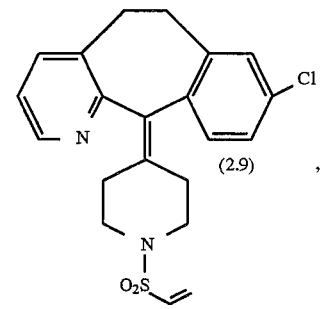

(2.9)

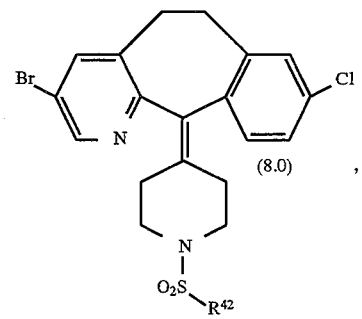

(8.0)

73
-continued
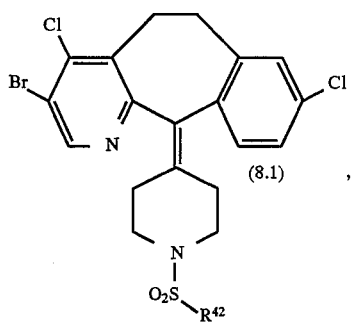
(8.1)
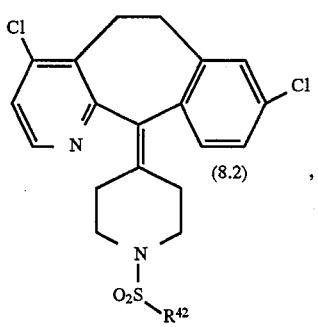
(8.2)
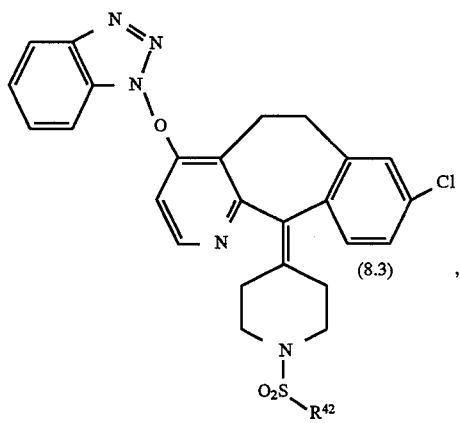
(8.3)
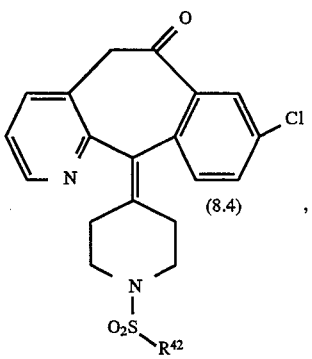
(8.4)
74
-continued
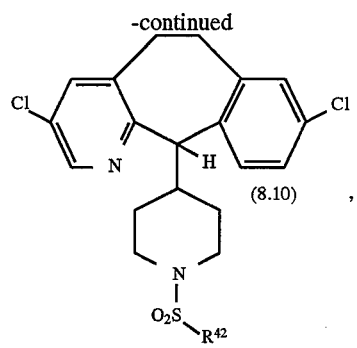
(8.10)
or
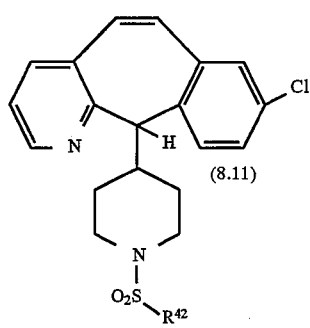
(8.11)
wherein $R^{42}$ is selected from:
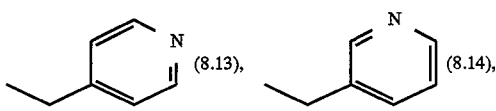 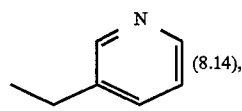
(8.13), (8.14),
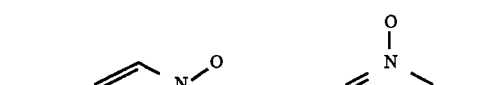 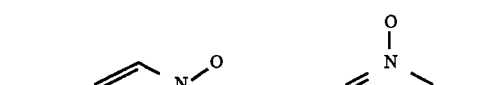
(8.15), (8.16),
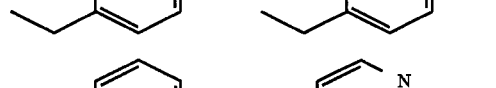 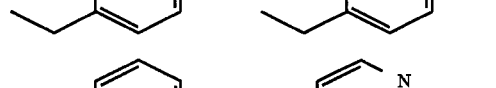
(8.17), (8.18),
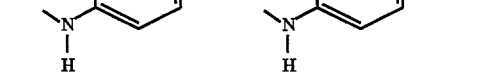 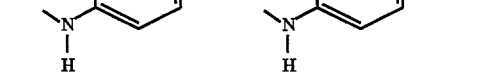
(8.19), (8.20),
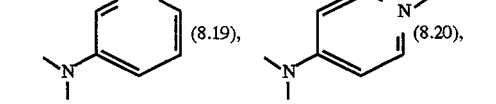 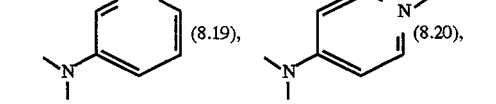
(8.21), (8.22),
or -continued

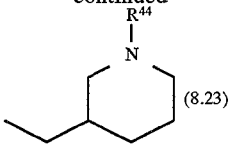

wherein $R^{44}$ is selected from H, alkyl, alkylcarbonyl, Lkoxycarbonyl or —C(O)NHR$^{10}$ wherein $R^{10}$ is H or alkyl.

15. A pharmaceutical composition for inhibiting farnesyl protein transferase comprising an effective amount of a compound of claim 7 in combination with a pharmaceutically acceptable carrier.

16. The compound of claim 7 selected from:

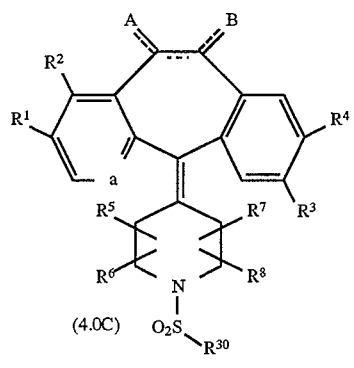

or

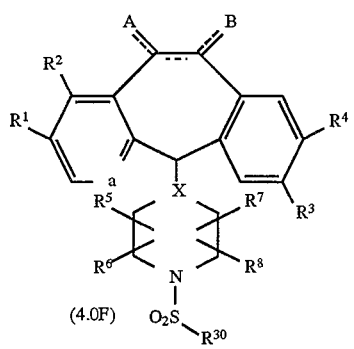

17. A method for inhibiting farnesyl protein transferase in a patient in need of such treatment comprising administering an effective amount of a compound of Formula 1.0:

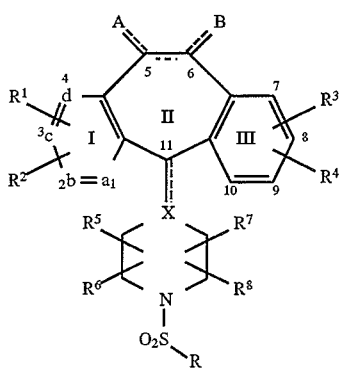

or a pharmaceutically acceptable salt or solvate thereof, wherein:

a is N;

b, c, and d are C;

$R^1$ and $R^2$ are the same or different and each independently represents H, benzotriazol-lyloxy, $C_1$ to $C_4$ alkyl or ahlo;

$R^3$ and $R^4$ are independently H or halo;

$R^5$, $R^6$, $R^7$ and $R^8$ each represent H;

X represents N or C, which C may contain an optional double bond to carbon atom 11;

the dotted lines represent optional double bonds;

the dotted line between carbon atoms 5 and 6 represents an optional double bond, such that when a double bond is present, A and B independently represent H, and when no double bond is present between carbon atoms 5 and 6, A and B each independently represent $H_2$;

R is selected from the group consisting of:

(1) $C_1$ to $C_4$ alkyl;

(2) phenyl substituted with 1 to 3 substituents selected from $R^1$, $R^2$ or C(O)OR$^{20}$, wherein $R^{20}$ is selected from the group consisting of: $C_1$ to $C_6$ alkyl and H;

(3) bridged polycyclic hydrocarbons selected from adamantyl, norbonyl or norcamphoryl;

(4) substituted bridged polycyclic hydrocarbons, wherein the bridged unsubstituted polycyclic hydrocarbon is selected from adamantyl, norbornyl or norcamphoryl, wherein the substituents are selected from the group consisting of $C_1$ to $C_6$ alkyl, said substituted bridged polycyclic hydrocarbon having from 1 to 8 substituents, and each substituent being the same or different;

(5) —(CH)$_2$R$^{21}$ wherein $R^{21}$ is $C_6$ to $C_{15}$ aryl, heteroaryl wherein said heteroaryl has at least one heteroatom selected from O, S, or N and has from 2 to 14 carbon atoms, 2-,3- or 4-piperidyl or N-substituted piperidyl, wherein the substituent on said N-substituted piperidyl is $C_1$ to $C_4$ alkyl, alkylcarbonyl or —C(O)NH(R$^{10}$) wherein $R^{10}$ is H or alkyl, a bridged polycyclic hydrocarbon selected from adamantyl, norbornyl or norcamphoryl, or a substituted bridged polycyclic hydrocarbon wherein the bridged unsubstituted polycyclic hydrocarbon is selected from adamantyl, norbornyl or norcamphoryl and wherein the substituents are selected from the group consisting of $C_1$ to $C_6$ alkyl and wherein said substituted bridged polycyclic hydrocarbon having from 1 to 8 substituents, and each substituent being the same or different;

(6) heteroaryl wherein said heteroaryl has at least one heteroatom selected from O, S, or N and has from 2 to 14 carbon atoms;

(7) substituted hetero aryl wherein said substituents are selected from the group consisting of: $C_1$ to $C_6$ alkyl and —NHC(O)R$^{22}$ wherein $R^{22}$ is a $C_1$ to $C_6$ alkyl and wherein said heteroaryl has at least one heteroatom selected from O, S, or N and has from 2 to 14 carbon atoms;

(8) $C_2$ to $C_6$ alkenyl; and (9) —N(R$^{23}$)$_2$ wherein each $R^{23}$ is independently selected from the group consisting of: $C_1$ to $C_6$ alkyl, H, $C_6$ to $C_{15}$ aryl, 2-,3- or 4-piperidyl or N-substituted piperidyl, wherein the substituent on said N-substituted piperidyl is $C_1$ to $C_4$ alkyl, alkylcarbonyl or —C(O)NH(R$^{10}$) wherein $R^{10}$ is H or alkyl, heteroaryl wherein said heteroaryl has at least one heteroatom selected from O, S, or N and has from 2 to 14 carbon atoms, each $R^{23}$ is selected such that there is no more than one H bound to the nitrogen.

18. The compound of claim 7 wherein:

a is N;

b, c, and d are C;

$R^1$ and $R^2$ are the same or different and each independently represents H, benzotriazol-1yloxy, $C_1$ to $C_4$ alkyl or halo;

$R^3$ and $R^4$ are independently H or halo;

$R^5$, $R^6$, $R^7$ and $R^8$ each represent H;

X represents N or C, which C may contain an optional double bond to carbon atom 11;

the dotted lines represent optional double bonds; and the dotted line between carbon atoms 5 and 6 represents an optional double bond, such that when a double bond is present, A and B independently represent H, and when no double bond is present between carbon atoms 5 and 6, A and B each independently represent $H_2$.

19. The method of claim 1 wherein: said aryl for said $R^{21}$ in subparagraph (5) is selected from phenyl or phenyl substituted with 1 to 3 groups selected from halo, alkyl, haloalkyl or alkoxy; said heteroaryl for said $R^{21}$ in subparagraph (5) is selected from thiophene, thiazole, pyridyl or pyridyl N-oxide; said heteroaryl in subparagraphs (6) and (7) is selected from thiophene, thiazole, pyridyl or pyridyl N-oxide; said aryl for said $R^{23}$ in subparagraph (9) is selected from phenyl or substituted phenyl; and said heteroaryl for said $R^{23}$ in subparagraph (9) is selected from pyridyl, 3-pyridyl N-oxide or 4-pyridyl N-oxide.

20. The compound of claim 7 wherein: said heteroaryl for said $R^{23}$ in subparagraph (3) is selected from thiophene, thiazole, pyridyl or pyridyl N-oxide; said heteroaryl in subparagraphs (4) and (5) is selected from thiophene, thiazole, pyridyl or pyridyl N-oxide; said aryl for said $R^{40}$ in subparagraph (7) is selected from phenyl or substituted phenyl; and said heteroaryl for said $R^{40}$ in subparagraph (7) is selected from pyridyl, 3-pyridyl N-oxide or 4-pyridyl N-oxide.

21. The compound of claim 12 wherein said heteroaryl for said $R^{32}$ is selected from thiophene, thiazole, pyridyl or pyridyl N-oxide.

22. The compound of claim 7 wherein the compound is selected from the group consisting of:

(8.5)

and

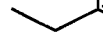

wherein $R^{42}$ is selected from:

-continued

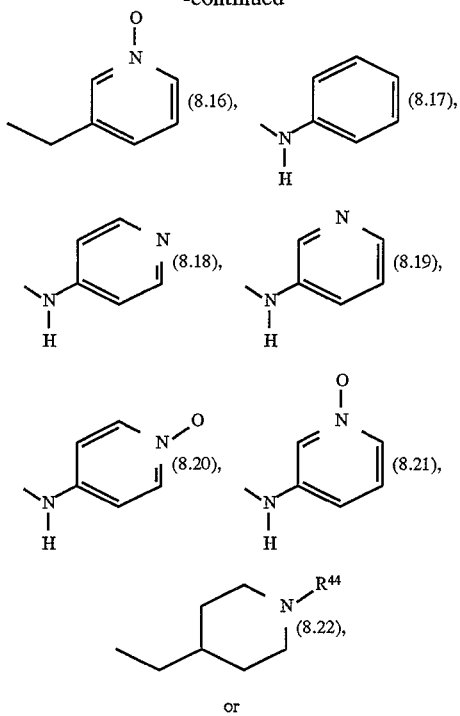

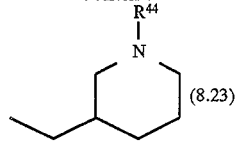

wherein $R^{44}$ is selected from H, alkyl, alkylcarbonyl, alkoxycarbonyl or —C(O)NHR$^{10}$ wherein $R^{10}$ is H or alkyl.

23. The compound of claim 7 wherein:

a is N;

b, c, and d are C;

$R^1$ and $R^2$ are the same or different and each independently represents H, benzotriazol-1yloxy, $C_1$ to $C_4$ alkyl or halo;

$R^3$ and $R^4$ are independently H or halo;

$R^5$, $R^6$, $R^7$ and $R^8$ each represent H; and the dotted line between carbon atoms 5 and 6 represents an optional double bond, such that when a double bond is present, A and B independently represent H, and when no double bond is present between carbon atoms 5 and 6, A and B each independently represent H2.

* * * * *